(12) United States Patent
Sachs et al.

(10) Patent No.: US 6,906,320 B2
(45) Date of Patent: Jun. 14, 2005

(54) MASS SPECTROMETRY DATA ANALYSIS TECHNIQUES

(75) Inventors: Jeffrey R. Sachs, Basking Ridge, NJ (US); Matthew C. Wiener, Westfield, NJ (US); Nathan A. Yates, Piscataway, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/814,474

(22) Filed: Mar. 31, 2004

(65) Prior Publication Data

US 2004/0195500 A1 Oct. 7, 2004

Related U.S. Application Data

(60) Provisional application No. 60/459,813, filed on Apr. 2, 2003.

(51) Int. Cl.[7] .......................... H01J 49/00; G06F 19/00
(52) U.S. Cl. ....................... 250/282; 436/173; 702/23
(58) Field of Search .......................... 250/282; 702/23; 436/173

(56) References Cited

U.S. PATENT DOCUMENTS

| | | | |
|---|---|---|---|
| 6,188,064 B1 * | 2/2001 | Koster | 250/282 |
| 6,393,367 B1 * | 5/2002 | Tang et al. | 436/173 |
| 2002/0063208 A1 | 5/2002 | Hastings | |
| 2002/0095260 A1 | 7/2002 | Huyn | |
| 2003/0040123 A1 | 2/2003 | Hastings | |
| 2003/0078739 A1 | 4/2003 | Norton et al. | |
| 2003/0111596 A1 | 6/2003 | Becker et al. | |
| 2004/0096982 A1 * | 5/2004 | Barnea et al. | 436/173 |

FOREIGN PATENT DOCUMENTS

| | | |
|---|---|---|
| AU | 199742988 | 3/1998 |
| WO | WO 02/42427 | 5/2002 |
| WO | WO 02/44715 | 6/2002 |
| WO | WO 02/077207 | 10/2002 |

OTHER PUBLICATIONS

Andersen, J. et al. "Proteomic characterization of the human centrosome by protein correlation profiling", Nature, 2003, vol. 426, pp. 570–574.

Ball, G. et al. "An integrated approach utilizing artificial neural networks and SELDI mass spectrometry for the classification of human tumours and rapid identification of potential biomarkers", Bioinformatics, 2002, vol. 18, pp. 395–404.

Banez, L. et al. "Diagnostic Potential of Serum Proteomic Patterns in Prostate Cancer", The Journal of Urology, 2003, vol. 170, pp. 442–446.

Chelius, D. et al. "Quantitative Profiling of Proteins in Complex Mixtures Using Liquid Chromatography and Mass Spectrometry", Journal of Proteome Research, 2002, vol. 1, pp. 317–323.

Fang, J. et al. "Quadratic Detectors for Enegery Estimation", IEEE Trans. Signal Processing, 1995, vol. 43, pp. 2582–2594.

Flory, M. et al. "Advances in quantitative proteomics using stable isotope tags", Trends in Biotechnology, 2002, vol. 20, No. 12 (Suppl.), pp. S23–S29.

(Continued)

*Primary Examiner*—Jack I. Berman
(74) *Attorney, Agent, or Firm*—Sheldon O. Heber; Jack L. Tribble

(57) ABSTRACT

The present invention features mass spectrometry data analysis techniques that can be employed to selectively identify analytes differing in abundance between different sample sets. The employed techniques determine the statistical significance of changes to signals associated with mass-to-charge ratios ("m/z-intensity pairs") between individual samples and sample sets. Based on the statistical significance, changes likely to indicate analyte level differences are identified. Based on intensities of the signals, ratios of analyte abundances can be determined.

34 Claims, 20 Drawing Sheets

OTHER PUBLICATIONS

Frank, R. et al. "Clinical Biomarkers in Drug Discovery and Development", Nature, 2003, vol. 2, pp. 566–580.

Friedman, D. et al. "Proteome analysis of human colon cancer by two–dimensional difference gel electrophoresis and mass spectrometry", Proteomics, 2004, vol. 4, pp. 793–811.

Gillespie, B. et al. "Optimizing Time–Frequency Kernels for Classification", IEE Transactions of Signal Processing, 2001, vol. 49, pp. 485–496.

Glish, G. et al. "The Basics of Mass Spectrometry in the Twenty–First Century", Nature, 2003, vol. 2, pp. 140–150.

Hastings, C. et al. "New algorithms for processing and peak detection in liquid chromatography/mass spectrometry data", Rapid Communications in Mass Spectrometry, 2002, vol. 16, pp. 462–467.

Idborg–Bjorkman, H. et al. "Screening of Biomarkers in Rat Urine Using LC/Electrospray Ionization–MS and Two–Way Data Analysis", Analytical Chemistry, 2003, vol. 75, pp. 4784–4792.

Issaq, H. et al. "SELDI–TOF MS for Diagnostic Proteomics", Analytical Chemistry, 2003, vol. 75, pp. 149A–155A.

Juang, B. et al. "On the Use of Bandpass Liftering in Speech Recognition", 1987, vol. ASSP–35, pp. 947–954.

Lee, Y. et al. "Protein chips: from concept to practice", Trends in Biotechnology, 2002, vol. 20, No. 12 (Suppl.), pp. S14–S18.

Lieberman, S. et al. "Identification of the β cell antigen targeted by a prevalent population of pathogenic CD8+ T cells in autimmune diabetes", Proc. Natl. Acad. Sci. USA, 2003, vol. 100, pp. 8384–8388.

Lim, C. et al. "Current Developments in LC–MS for Pharmaceutical Analysis", Biol. Pharm. Bull., 2002, vol. 25, pp. 547–557.

Link, A. et al. "Direct analysis of protein complexes using mass spectrometry", 1999, Nature Biotechnology, vol. 17, pp. 676–682.

Link, A. "Multidimensional peptide separations in proteomics", Trends in Biotechnology, 2002, vol. 20, No. 12 (Suppl.) pp. S8–S13.

Naureckiene, S. et al. "Identification of *HEL* as the Second Gene of Niemann–Pick C Disease", Science, 2000, vol. 290, pp. 2298–2301.

Ong, S. et al. "Mass spectrometric–based approaches in quantitative proteomics", Methods, 2003, vol. 29, pp. 124–130.

Ong, S. et al. "Properties of 13C–Substituted Arginine in Stable Isoptope Labeling by Amino Acids in Cell Culture (SILAC)", Journal of Proteome Research, 2003, vol. 2, pp. 173–181.

Ong, S. et al. "Stable Isotope Labeling by Amino Acids in Cell Culture, SILAC, as a Simple and Accurate Approach to Expression Proteomics", Molecular & Cellular Proteomics, 2002, vol. 1, pp. 376–386.

Pauler, D. et al. "Predicting time to prostate cancer recurrence based on joint models for non–linear longitudinal biomarkers and event time outcomes", Statistics in Medicine, 2002, vol. 21, pp. 3897–3911.

Petriconin, E. et al. "Proteomic analysis at the bedside: early detection of cancer", Trends in Biotechnology, 2002, vol. 20, No. 12 (Suppl.), pp. S30–S34.

Petricoin, E. et al. "Serum Proteomic Patterns for Detection of Prostate Cancer", Journal of the National Cancer Institute, 2002, vol. 94, pp. 1576–1578.

Petricoin, E. et al. "Use of proteomic patterns in serum to identify ovarian cancer", The Lancet, 2002, vol. 359, pp. 572–577.

Pitton, J. et al. "Discrete–Time Implementation of the Cone–Kernel Time–Frequency Representation", IEEE Trans. Signal Processing, 1995, vol. 43, pp. 1996–1998.

Qu, Y. et al. "Boosted Decision Tree Analysis of Surface–enhanced Laser Desorption/Ionization Mass Spectral Serum Profiles Discriminates Prostate Cancer from Noncancer Patients", Clinical Chemistry, 2002, vol. 48, pp. 1835–1843.

Ryan, T. et al. "Proteomics: drug target discovery on an industrial scale", Trends in Biotechnology, 2002, vol. 20, No. 12 (Suppl.), pp. S45–S51.

Sechi, S. et al. "Quantitative proteomics using mass spectrometry", Current Opinion in Chemical Biology, 2003, vol. 7, pp. 70–77.

Sidransky, D. et al. "Serum Protein MALDI Profiling to Distinguish Upper Aerodigestive Tract Cancer Patients From Control Subjects", Journal of the National Cancer Institute, 2003, vol. 95, pp. 1711–1717.

Smith, R. "Trends in mass spectrometry instrumentation for proteomics", Trends in Biotechnology, 2002, vol. 20, No. 12 (Suppl.), pp. S3–S7.

Tammen, H. et al. "Expression profiling of breast cancer cells by differential peptide display", Breast Cancer Research and Treatment, 2003, vol 79, pp. 83–93.

Tao, W. et al. "Advances in quantitative proteomics via stable isotope tagging and mass spectrometry", Current Opinion in Biotechnology, 2003, vol. 14, pp. 110–118.

Uchida, T. et al. "Application of a Novel Protein Biochip Technology for Detection and Identification of Rheumatoid Arthritis Biomarkers in Synovial Fluid", Journal of Proteome Resarch, 2002, vol. 1, pp. 495–499.

Wang, W. et al. "Quantification of Proteins and Metabolites by Mass Spectrometry without Isotopic Labeling or Spiked Standards", Analytical Chemistry, 2003, vol. 75, pp. 4818–4826.

Wiener, M. et al. "Differential Mass Spectrometry: A Label–Free LC–MS Method for Finding Significant Differences in Complex Peptide and Protein Mixtures", Analytical Chemistry, 2004, vol. 76, pp. 6085–6096.

Ye, B. et al. "Haptogloblin–α Subunit As Potential Serum Biomarker in Ovarian Cancer: Identification and Characterization Using Proteomic Profiling and Mass Spectrometry", Clinical Cancer Research, 2003, vol. 9, pp. 2904–2911.

Zhu, W. et al. "Detection of cancer–specific markers amid massive mass spectral data", Proc. Natl. Acad. Sci. USA, 2003, vol. 100, pp. 14666–14671.

Caprion Pharmaceuticals, Inc., Presentation to Merck, Feb. 14, 2003.

\* cited by examiner

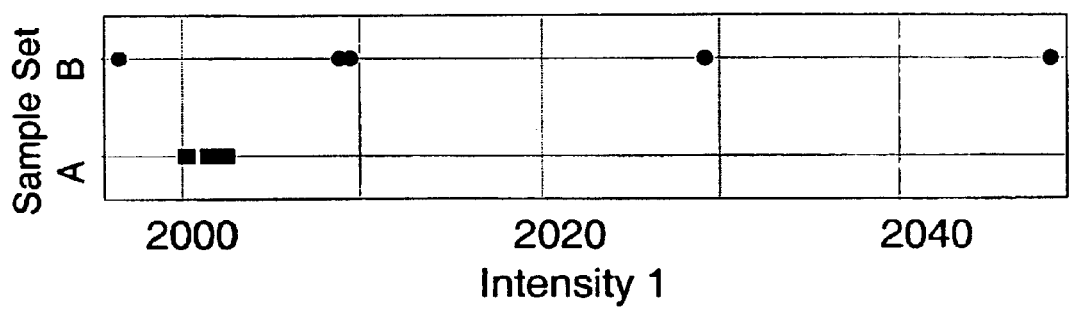
Figure 14A. No significant difference between sample sets A and B in means by t-test: p-value 0.131
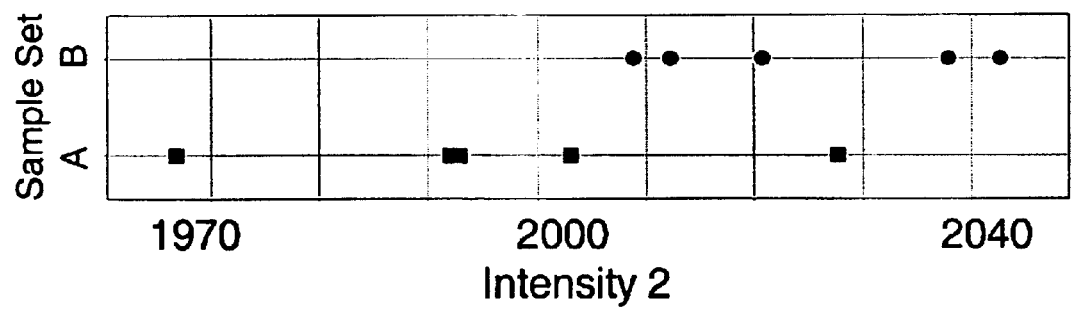
Figure 14B. No significant difference between sample sets A and B in means by t-test: p-value 0.0506

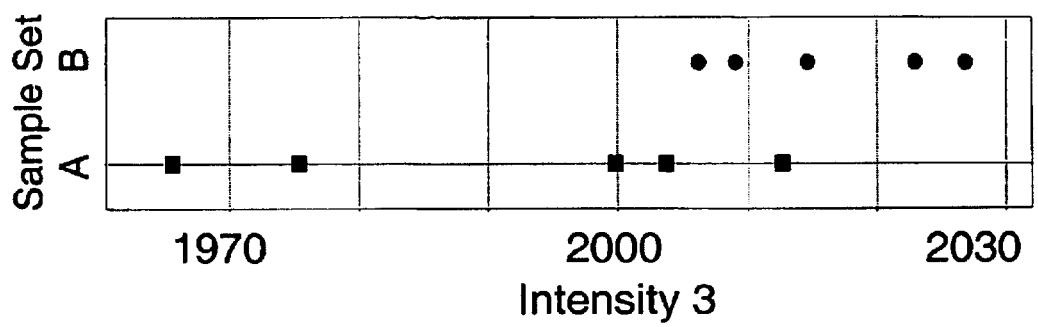
Figure 14C. Significant difference between sample sets A and B in means by t-test: p-value 0.0499
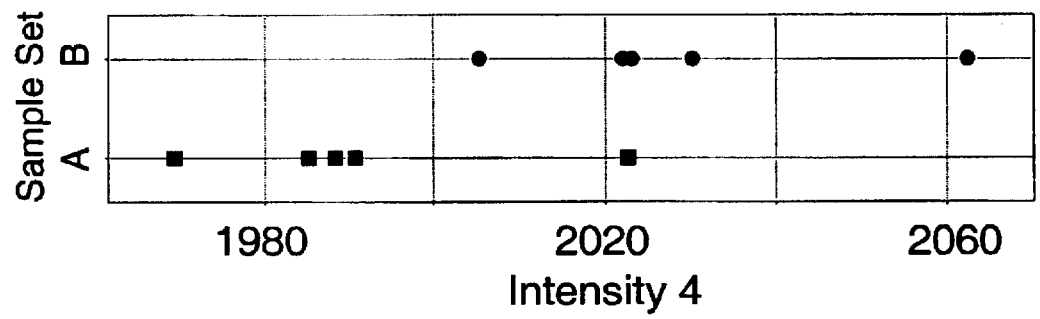
Figure 14D. Significant difference between sample sets A and B in means by t-test: p-value 0.0194

MASS SPECTROMETRY DATA ANALYSIS TECHNIQUES

CROSS-REFERENCE TO RELATED APPLICATIONS

The present application claims the benefit of U.S. Provisional Application No. 60/459,813, filed Apr. 2, 2003, hereby incorporated by reference herein.

BACKGROUND OF THE INVENTION

The references cited throughout the present application are not admitted to be prior art to the claimed invention.

Mass spectrometry is capable of detecting large numbers of analytes in complex mixtures. A wide range of different analytes can be detected including those of environmental and biological importance.

Peptides are an example of biologically important analytes. Peptides such as proteins interact in complex ways to regulate cellular functions. Small changes in the abundance of particular proteins or their modifications can significantly alter the functioning of a cell, can impact on the overall health of an animal, and can provide an indication as to the health of a cell or animal.

Proteomic studies measuring peptide expression are increasingly making use of mass spectrometry. (Smith, *Trends in Biotechnology* 20(12, *Suppl*):S3–S7, 2002.)

SUMMARY OF THE INVENTION

The present invention features mass spectrometry data analysis techniques that can be employed to selectively identify analytes differing in abundance between different sample sets. The employed techniques determine the statistical significance of changes to signals associated with mass-to-charge ratios ("m/z-intensity pairs") between individual samples and sample sets. Based on the statistical significance, changes likely to indicate analyte level differences are identified. Based on intensities of the signals, ratios of analyte abundances can be determined.

Variability in signal at a given m/z due to factors other than changes in analyte levels between sample sets is treated as noise. Noise can include biological or chemical variation within each sample set, and intrinsic variability in measurements made by the instrument.

A "sample set" is a collection of one or more samples that are grouped together for analytical purposes. A particular grouping generally involves samples having one or more common properties. Common properties include, for example, the location from where the sample was obtained, known attributes of the sample or source of the sample, and experimental conditions.

A sample set can be a "standard", which does not contain any analytes or contains a known amount of known analytes. The standard can be compared to a different sample set to determine whether the different sample set contains particular analytes.

Thus, a first aspect of the present invention features a mass spectrometry-based method for identifying differences in the level of one or more analytes between two or more sample sets. The method comprises the steps of:

a) obtaining spectra for individual samples for two or more sample sets, wherein a spectrum comprises m/z-intensity pairs, wherein an m/z intensity pair comprises an m/z identifier and a signal associated with the m/z identifier, b) for each m/z identifier of one or more m/z identifiers from the m/z intensity pairs, determining a relationship between the corresponding signals in those spectra, and c) assigning each relationship a rank or value based on both within-sample-set and between-sample-set signal distributions, wherein the rank or value is a measure of a likelihood that the signal arises from an analyte having a different level between the sample sets. Step (c) evaluates the statistical significance of the relationship.

Another aspect of the present invention features a computer program for analyzing spectra to identify differences in the level of one of more analytes between two or more sample sets. The program provides instructions on a computer readable medium for performing analyses described herein.

The m/z-identifier(s) and, if there are any, index variable value(s) corresponding to differences in the level of one or more analytes are said to "identify" the analyte(s). Analytes identified in this way can be further characterized by other analysis methods such as tandem mass spectrometry, database search, and chemical analysis. The relative abundance of identified analytes can also be quantified.

An "indexed spectrum" is the set of m/z-intensity pairs and corresponding index variable values obtained for a sample. Examples include data obtained by performing LC-MS (including, for example, high performance liquid chromatography-MS, reverse and normal phase chromatography-MS, ultra high pressure liquid chromatography-MS, size exclusion chromatography-MS, anion or cation exchange chromatography-MS, electrophoresis-MS, and capillary zone electrophoresis-MS), multi-dimensional LC-MS, multidimensional-LC-$MS^n$, GC-MS (Gas-chromatography-MS), gas phase ion mobility-MS, or other hybrid-MS procedure one time on a single sample. Examples of index variables include: chromatographic separation time, affinity for one or more other analytes, biological activity or readout (e.g. Chromium release assay), solubility in one or more different solutions, mobility in various media, isoelectric point, temperature, and concentrations of reactants or therapeutic agents.

An "optionally indexed spectrum" is a spectrum that may or may not have one or more index variables. Except when stated otherwise, the terms "spectrum" and "spectra" will refer to "optionally indexed spectrum" and "optionally indexed spectra". The term "spectra set" refers to the collection of optionally indexed spectra obtained for a sample set. One example of data with no index variables is that generated by MALDI (Matrix Assisted Laser Deionization) mass spectrometry.

An m/z-intensity pair has an "intensity" (or "signal") and a mass-to-charge "identifier". An m/z-intensity pair is sometimes referred to as a mass spectrum "peak".

Intensity is any measure reflecting the number of ions detected. Examples of such measures include counts, ion counts, counts per second, and relative abundance. The intensity includes contributions of both noise and analyte components. In any particular case the noise or analyte components could be zero.

The mass-to-charge "identifier" can be any quantity that can be converted to or derived from one or more mass-to-charge ratios ("m/z") or measures related to m/z. Examples of measures related to m/z include molecular weight, monoisotopic mass, average mass, flight times, resonant frequencies, characteristic frequencies, scanning voltage, or scanning frequency.

The conversion of the m/z values to identifiers might be a many to one function that nonetheless maps, to distinct m/z values, m/z values that the user wishes to distinguish from one another. Examples of such functions include centroiding, rounding to a specified precision, median, mean, or geometric mean over sets of non-overlapping values, binning, or arbitrary identifiers.

If more than one m/z value is mapped to a particular identifier, the signals corresponding to the subset of m/z values mapped to that identifier could be combined using a user selected function. This function could be, for example, summation, convolution, median, geometric mean, or log mean.

The "rank or value" provides a statistical measure of the significance of a signal that varies between spectra sets. The rank or value could, for example, be a value from a statistical test or the rank of a p-value in a set of p-values, or the rank of a difference in a set of differences, or a log likelihood, or any monotone function of such values.

In different embodiments, the relationship is determined for at least 10, at least 100, at least 1,000, at least 10,000, at least 100,000, at least 1,000,000, at least 10,000,000 m/z identifiers; each m/z identifier is deterministically specified prior to step (b) above; and/or the relationships are found using a number of computations that grows at most polynomially, at most quadratically, or at most linear times log linearly in the number of m/z identifiers and/or in the number of distinct, used index variable values. Other embodiments are described herein.

"Central tendency", as used in this document, includes mean or median or means or medians weighted by various other quantities, or robust estimators of central tendency such as trimmed mean or mean of values lying in a specified percentile range. Other statistical measures of central tendency are not excluded.

Unless particular terms are mutually exclusive, reference to "or" indicates either or both possibilities. Occasionally phrases such as "and/or" are used to highlight either or both possibilities.

Reference to open-ended terms such as "comprises" allows for additional elements or steps. Occasionally phrases such as "one or more" are used with or without open-ended terms to highlight the possibility of additional elements or steps.

Unless explicitly stated reference to terms such as "a" or "an" is not limited to one. For example, "a cell" does not exclude "cells". Occasionally phrases such as one or more are used to highlight the presence of a plurality.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

BRIEF DESCRIPTION OF THE DRAWINGS

FIG. 11 is a black and white representation where dark areas are higher in condition A and light is higher in condition B. This could also be represented using color, for example, where green indicates no significant difference; shades of blue and purple indicate mean higher in condition B; and shades of yellow and red, higher in condition A.

FIG. 12 is a black and white representation, where darker indicates significantly higher in condition B and lighter indicates significantly higher in condition A. This could also be represented using color, for example, where orange indicates no significant difference; more intense red indicates significantly higher in condition B; and yellow significantly higher in condition A.

FIG. 13 is a monochrome rendering of a color representation where difference magnitudes have a blue (small differences) or red (large differences) color; and significance is represented by intensity, pale (not significant) or intense (significant). In the monochrome representation the magnitude and significance dimensions are conflated, resulting in loss of information.

FIGS. 14A–D illustrate statistical comparisons for several sets of 5 numbers in each of two conditions.

DETAILED DESCRIPTION OF THE INVENTION

Figure 1A:
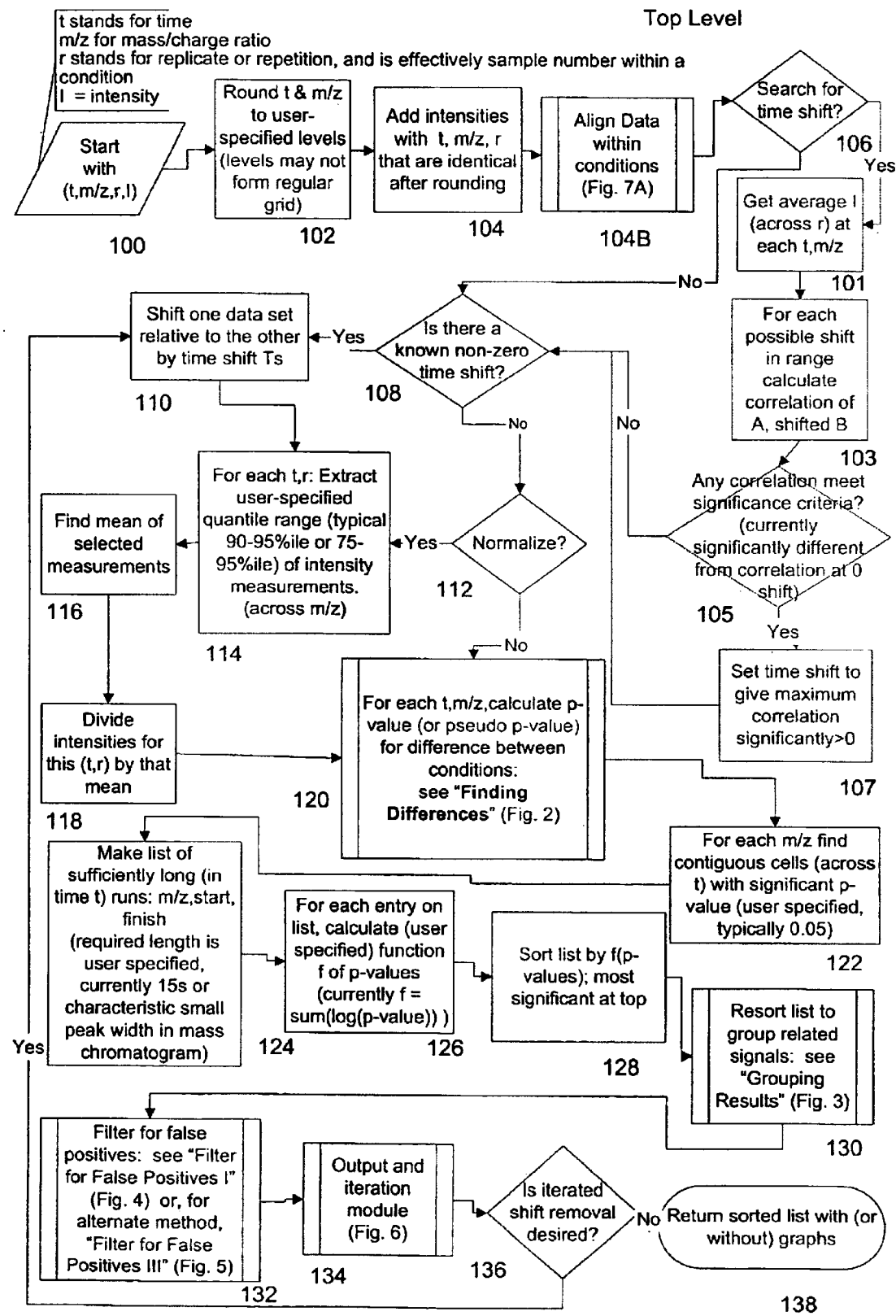
FIG. 1A illustrates steps for a preferred embodiment involving a time index.
Figure 1B:
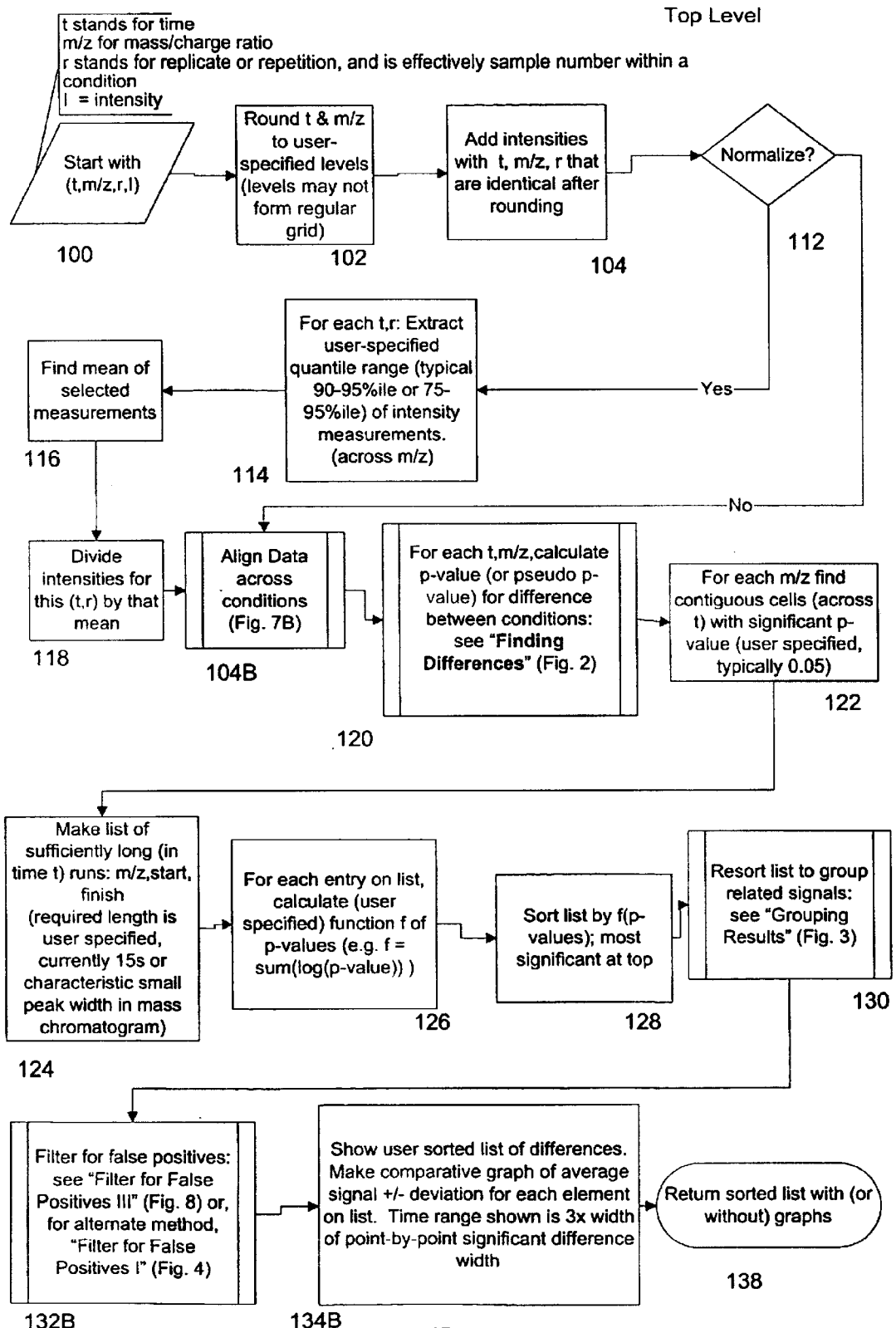
FIG. 1B illustrates steps for a preferred embodiment involving a time index with an alternate method for alignment.

The data analysis techniques described herein can be employed to selectively identify analytes differing in abundance between different sample sets. The employed techniques determine the statistical significance of changes in m/z-intensity pairs in spectra between individual samples and sample sets. Based on the statistical significance, changes likely to indicate analyte level differences are identified.

The mass spectrometry analysis techniques can be employed to accurately detect analyte changes in different samples, even analytes present in small amounts. The techniques are not dependent on special labels such as fluorescent, radioactive, affinity, isotopic, or covalent or associative chemical mass tagging or preparation. Though, such labels may be used to further increase sensitivity and specificity of the method or to otherwise change the attributes required to differentiate analytes between sample sets.

Generally, the sensitivity and specificity of the present method is independent of mixture complexity up to the resolution and dynamic range limitations of the instrumentation used to obtain spectra. When a normalization step is included in the calculations, the mixture complexity contributes only insofar as it changes the normalizing constants at each combination of index variables. Resolution of the instrument affects the outcome through possible ambiguity of m/z identifiers. Dynamic range of the instrument affects the outcome through possible ambiguity of measurements of signals near the extremes of the instrument's range.

I. Obtaining Data

Spectra for different sample sets can be obtained by performing one or more experiments or through other means such as journal publications or web or ftp sites providing such data. Spectra can be obtained to look at changes in different types of analytes and can, optionally, be indexed.

An "analyte" is a chemical entity. Examples of analytes include elements, compounds, complexes, and mixtures. Analytes may have physical or biological properties that can provide index variables such as one or more of following: chromatographic separation time, affinity for one or more other analytes, biological activity or readout (e.g. Chromium release assay), solubility in one or more different solutions, mobility in various media, isoelectric point, temperature, and concentrations of reactants or therapeutic agents. Index variables may be one or more continuous variables or one or more discrete ordered variables. The terms "index," or "indexes" or "indices" are also used herein to denote index variable or variables, respectively.

A. Mass Spectrometry

Mass spectrometry is a technique that measures m/z-intensity pairs of an ionizable substance. The m/z-intensity pair or pairs of an analyte provides a signature distinguishing the analyte from other substances having a different m/z-intensity pair or pairs.

The intensity of an analyte's m/z-intensity pair changes with the analyte's abundance within the response range of the instrument. Techniques and equipment for generating mass spectrometry data are well known in the art. Examples of ionization techniques that can be employed include electrospray ionization, matrix-assisted laser desorption/ionization, surface enhanced laser desorption/ionization, electron impact ionization, chemical ionization, and photo-ionization. (Glish et al., *Nature Review Drug Discovery* 2:140–150, 2003, Petricoin et al., *The Lancet* 359:572–577, 2002.) Examples of mass analyzers include Protein Biology System 2 SELDI-TOF mass spectrometer (Ciphergen Biosystems, Freemont Calif.), quadrupole mass filter, quadrupole ion trap mass spectrometer (ThermoFinnigan, San Jose, Calif.), triple-stage quadrupole mass spectrometer, time-of-flight mass spectrometer, Fourier-transform ion cyclotron resonance mass spectrometer, and hybrids of all of these.

In different embodiments signals might be transformed in different ways to improve the performance of the method. Either individual signals or summaries of the distributions of signals (such as mean or variance) might be so transformed. Possible transformations include taking the logarithm, taking some positive or negative power, for example the square root or inverse, or taking the arcsin (Myers, Classical and Modern Regression with Applications, $2^{nd}$ edition, Duxbury Press, 1990).

B. Sample Sets

A sample set contains one or more samples grouped together for analysis purposes. The grouping of a particular sample set and the selection of different sample sets can be chosen to perform numerous different types of analyses. Grouping can be decided before, during, or after collecting data Grouping may be dynamically decided based on data.

The analysis techniques described herein can be performed on different types of samples such as biological samples and environmental samples. Biological samples contain biological material. Biological samples can be obtained from different sources such as single-cell organisms or multi-cell organisms. Examples of multi-cell organisms include plants and animals.

An "animal" is a member of the animal kingdom. Preferably, the animal is a mammal, such as a human, a farm animal (e.g., cow, pig, horse, or chicken), a pet (e.g., cat or dog), or an animal that can be used as a model system (e.g., mouse, rat, guinea pig, dog, or monkey).

Biological material includes viral, cellular, or extracellular components, that are present in a virus, a single cell, or a multi-cell organism; and material secreted by cells and animals. Cellular material includes constituents of a cell in general and subcellular fractions.

Biological material that can be obtained from multi-cell organisms includes cellular material and material from other parts of multi-cell organisms. Examples of material from other parts of a multi-cell organism include, for example, tissue; biological fluid (e.g., blood, cerebrospinal fluid, urine, saliva, semen, lymph, feces, sweat, sputum, and mucus); excretions, exuded or secreted material; and/or preparations made from subparts such as liver, spleen, kidney, muscle, lung, heart, brain, or other organs or components of organs (e.g. amygdala, adrenal gland, or hippocampus).

Biologically important compounds include peptides, carbohydrates, lipids, nucleic acids, drugs, drug metabolites, and different derivatives thereof. A derivative thereof includes a modified substance or a fragment. For example, peptide derivatives includes fragments of a post- or co-translationally modified peptide.

A peptide is a preferred analyte for biological analysis. Reference to "peptide" indicates one or more amino acids joined together by a peptide bond, and does not provide a size or function limitation. Examples of peptides include enzymes, structural protein, and hormones.

Examples of different sample sets that are suited for analysis include the following:

1) Two or more sample sets each treated with a different amount of a particular compound, where one amount can be, for example, no compound;
2) Two or more sample sets each treated with a different compound or where one set is not treated with a compound;
3) Two or more sample sets each associated with different levels of a disease or disorder, where one level can be, for example, a healthy sample set;
4) Two or more sample sets exposed to a different type or level of environment stimulus, where one type or level can be, for example, the absence of the stimulus;
5) Two or more sample sets, where at least one sample set has a predetermined or known level (which may be, for example, a zero concentration) of one or more particular analytes and in at least one sample the abundance of at least one analyte is not known;
6) Two or more sample sets each differing by one or more phenotypes;
7) Two or more sample sets differing by one or more genes or by the expression or form of one or more genes;
8) Two or more sample sets subjected to different medical treatments, where one medical treatment may be a control;
9) Two or more sample sets evaluated at different times (for example, at different times after introduction of a chemical agent);
10) Two or more sample sets consisting of chemical mixtures (pure or complex) differing in synthesis or physical modification (e.g., covalent chemical, noncovalent chemical, radiological, electromagnetic, mechanical, or gravitational);
11) Two or more sample sets consisting of chemical mixtures (pure or complex) exposed to different levels (possibly including zero) of a biological material or other material (including for use in high throughput screening);
12) Two or more sample sets consisting of chemical mixtures (pure or complex) exposed to different levels (possibly including zero) of a biological material or other material that has, optionally, been chemically or physically modified (including for use in high throughput screening); and
13) Two or more sample sets derived from a single chemical mixture through a separation process, as could be obtained by collecting samples over different elution times from a chromatographic separation, or over other index variable ranges for other technologies. These samples could be physically isolated and then run through the processes as for the others listed above, or could be processed electronically, for example by transforming the elution times of an LC-MS run so that spectra from set of time ranges are compared with spectra from another set of time ranges. In the case where one of the time ranges is chosen to represent a "blank" sample through the use of a set of ranges deemed (by human or standard signal detection software) to have negligible quantities of analyte in it, the transformation could be to treat all spectra as if they were replicates measured at each time of interest, so that (for example) if the time range chosen to act as the "blank" had 100 measured spectra, each time in the time range would now be considered to have all 100 measured spectra in a "blank" condition.

Increasing the number of spectra taken on a sample set facilitates accurate detection of analyte level differences. The number of spectra can be increased by taking repeated spectra on each sample or some subset of the samples, by increasing the number of samples in one or both sample sets, or by a combination of these two. In different embodiments at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 30, and at least 40 different spectra are analyzed for each sample set.

Increasing the number of distinct samples may have the additional advantage of taking into account variability among different members of the sample set (as opposed to intrinsic variability in measurements made by the instrument). This may facilitate protocols for finding differences consistent across many members of the sample set. One application of such protocols is in distinguishing differences associated with a disease state such as cancer from other phenotypic differences represented in a population. In different embodiments the number of different samples in a sample set for which spectra are obtained is 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 30.

The method is illustrated in the Examples infra in which there are exactly two sample sets. Cases in which there are more than two sample sets can be analyzed by doing all pairwise analyses. In this case multidimensional generalizations of some of the tests demonstrated here can be used. For example, analysis of variance can be used instead of the t-test, and the Kruskal test can be used instead of the Wilcoxon rank sum test.

II. Analytical Techniques

Selective identification is performed by determining the statistical significance of differences in m/z-intensity pairs using both within-sample-set and between-sample-set m/z-intensity pair variability. The preferred way to obtain information about within-sample-set variability is to have multiple spectra in each set and measure variability directly. If multiple spectra are not available, it is possible to proceed using an assumed variance structure.

An assumed variance structure may be quantitative, based either on pre-existing data or on analysis of contiguous data points in the single available spectrum. It may also be qualitative, for example, assuming that the variance associated with any measurement is equal to some constant value (which need not be specified). Under this assumption the rank of detected differences based on a significance test is the same as the rank of detected differences based on the absolute value of the differences.

In general, one or more attributes of m/z-intensity pairs can be used to provide a relationship for determining statistical significance of signal variability. Examples include binned or smoothed signals and linearly or non-linearly filtered signals.

Different embodiments for identifying analytes differing in abundance between sample sets are illustrated by reference to the following steps: (A) Gridding the Data; (B)

Alignment; (C) Normalization; (D) Evaluating Differences; (E) Time-Persistence; (F) Re-Sorting; (G) Partitioning; (H) Re-Alignment; and (I) Sensitivity and Specificity. Step (D) illustrates techniques that can be employed to determine the significance of changes to an m/z-intensity pair within a spectra set and between spectra sets. Steps (A), (B), (C), (E), (F), (G), (H), and (I) provide examples of additional embodiments that can be performed.

Figure 2:
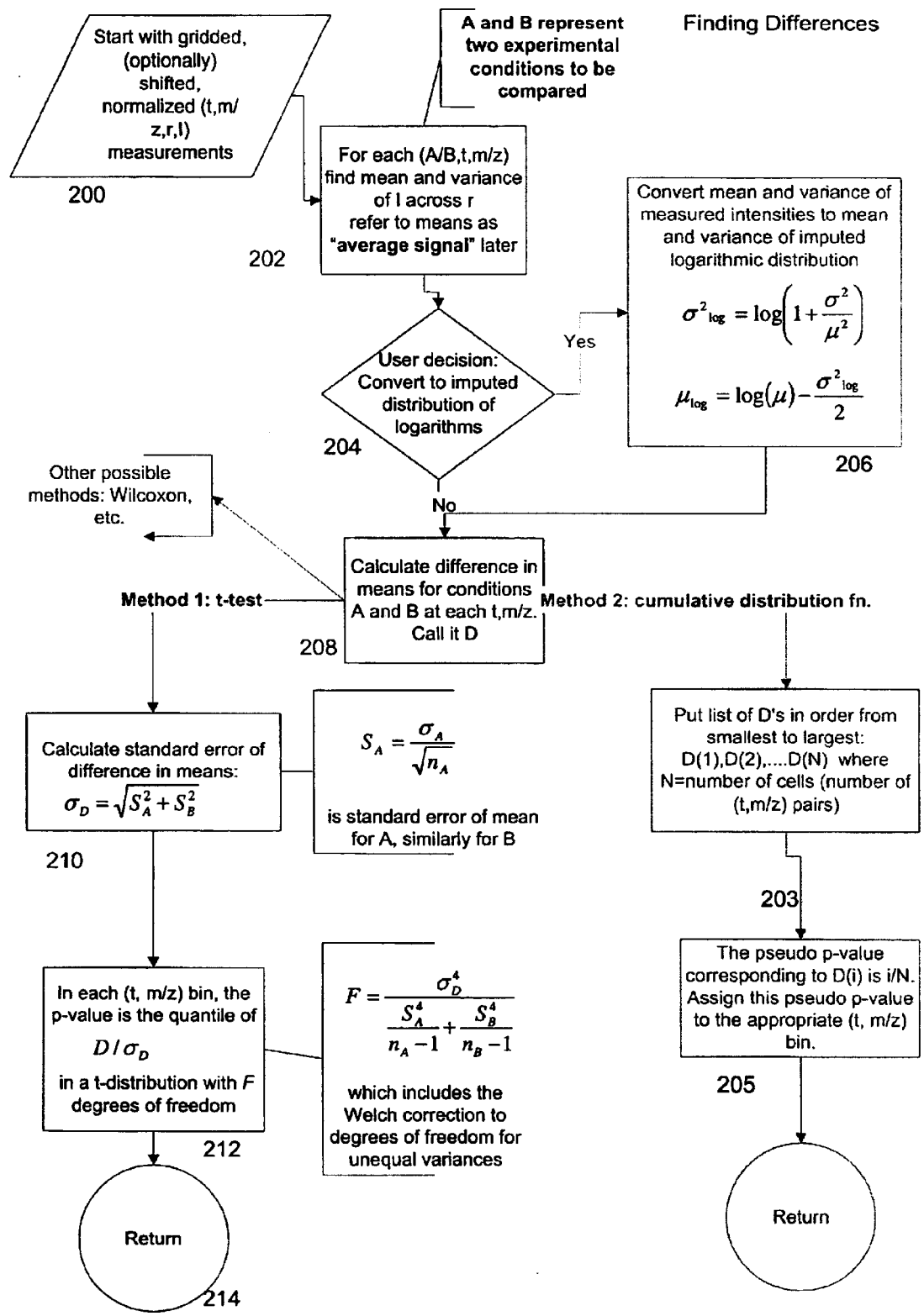
FIG. 2 provides an example of steps that can be used for "Finding Differences" in FIG. 1A or 1B.
Figure 3:
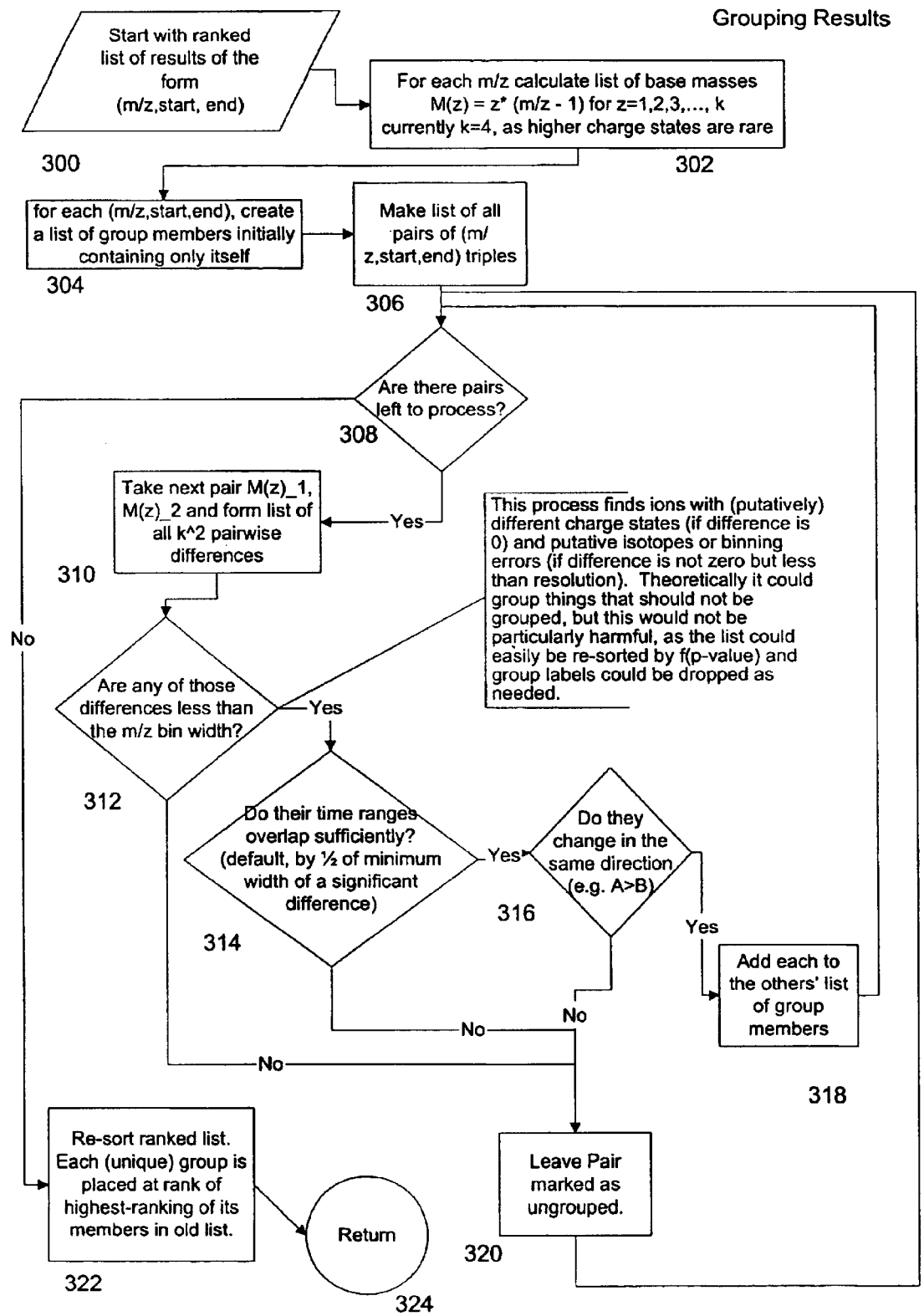
FIG. 3 provides an example of steps that can be used for "Grouping Results" in FIG. 1A or 1B.
Figure 4:
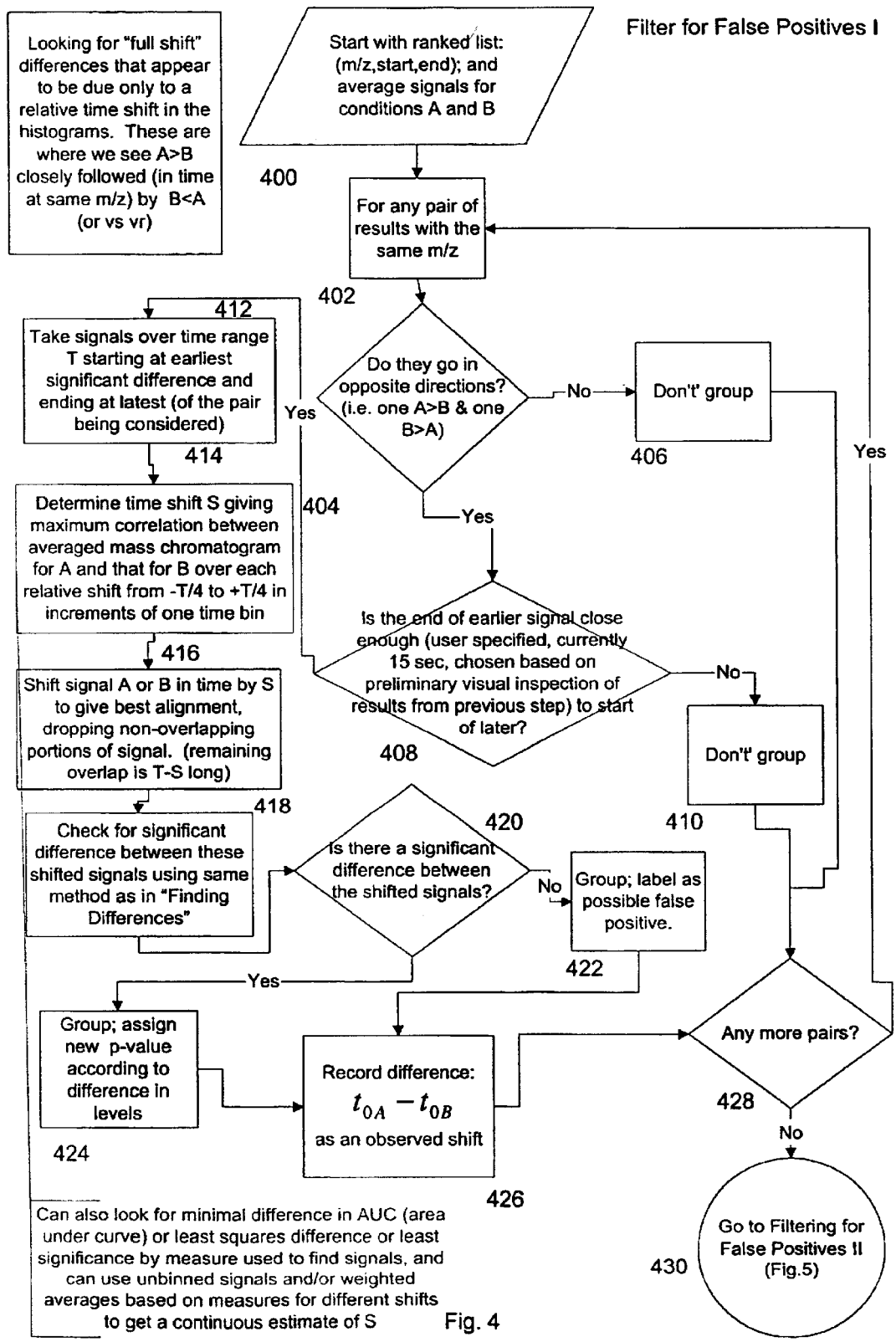
FIG. 4 provides an example of steps that can be used for "Filtering for False Positives I" in FIG. 1A or 1B. The illustrated steps can be employed to look for "full shift" differences that appear to be due only to a relative time shift in histograms. A full shift is defined as an occurrence of A>B closely followed in time at the same m/z by B<A.
Figure 5:
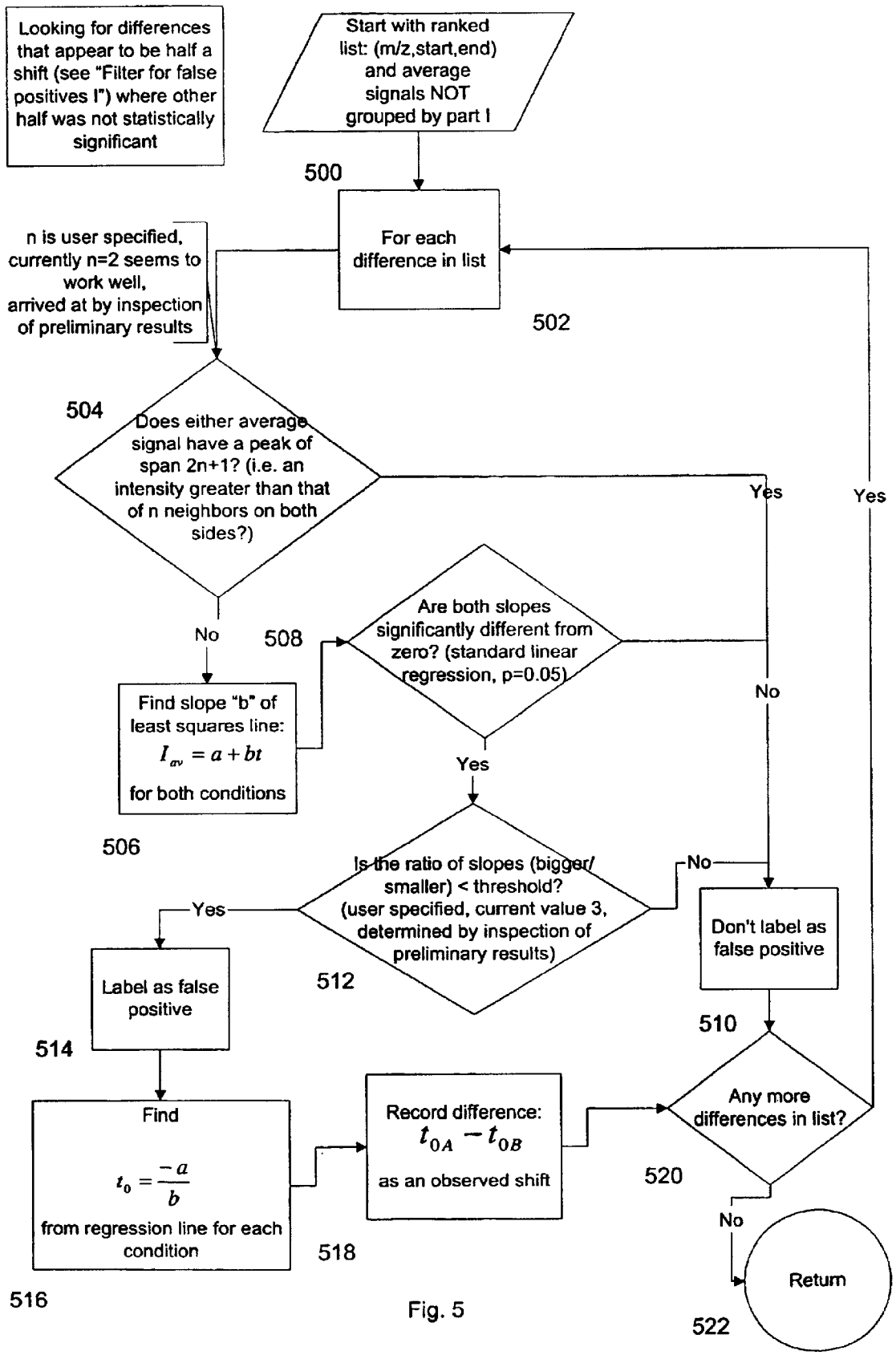
FIG. 5 provides an example of steps for "Filtering for False Positives II" illustrated in FIG. 4. The illustrated steps can be employed to look for false positives by examining half shift differences. A "half shift" arises in a situation in which only one half of a full shift (as in the previous paragraph) is detected as a statistically significant difference. In practice half shifts were found more frequently than full shifts.
Figure 6:
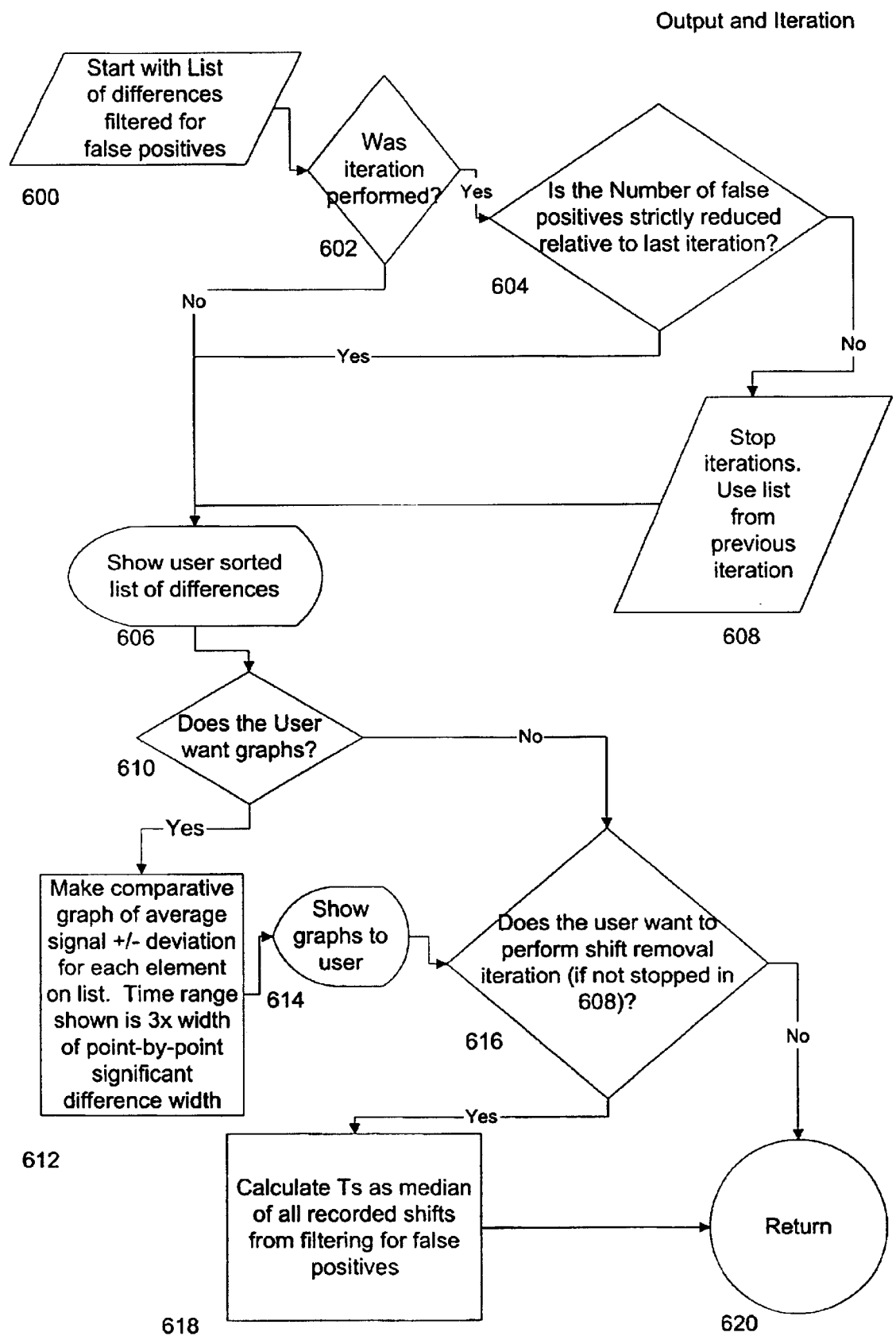
FIG. 6 provides an example of steps that can be used for the "Output and iteration module" illustrated in FIG. 1A.
Figure 7A:
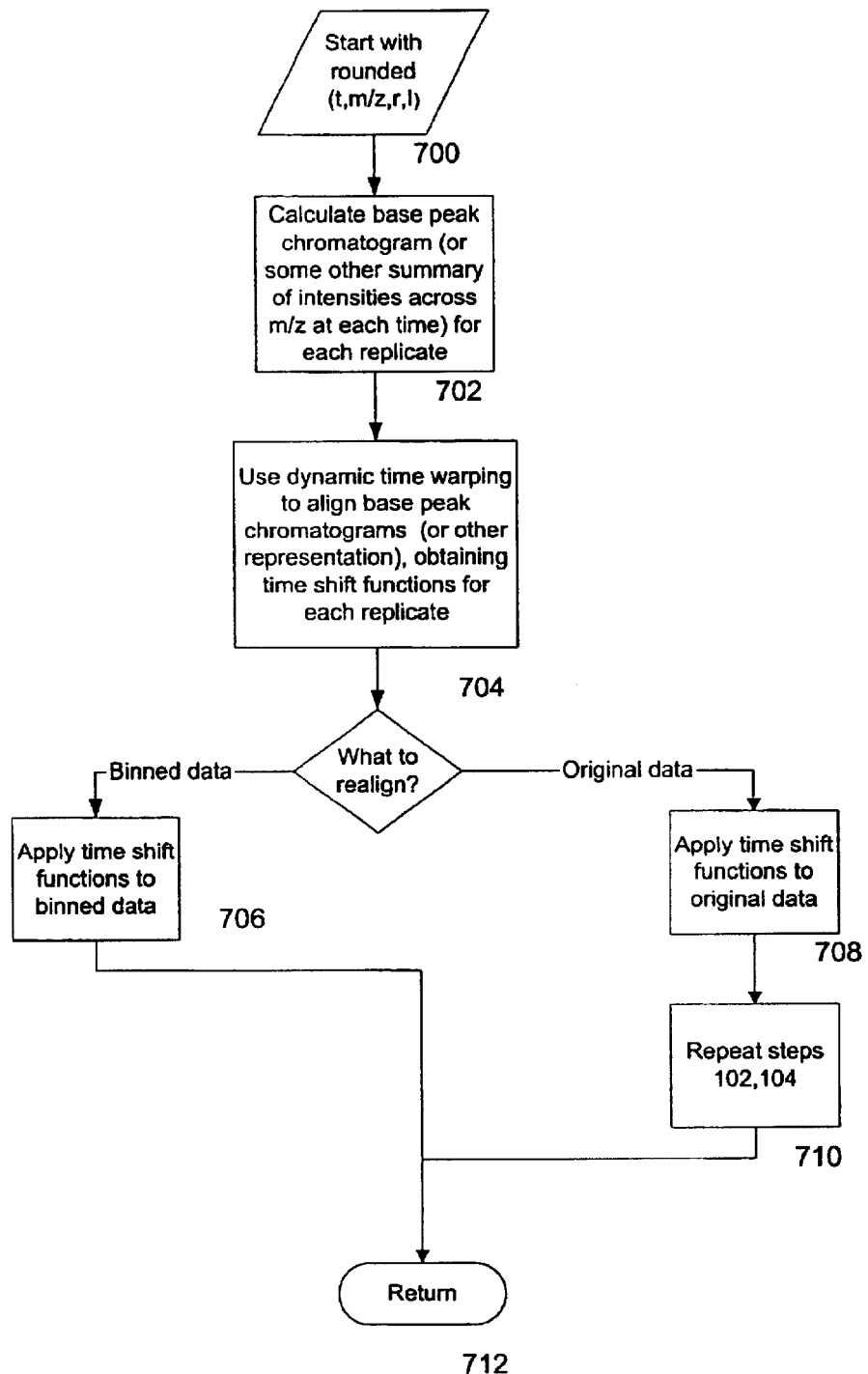
FIG. 7A provides an example of steps that can be used for the "Aligning Spectra Within Conditions" module illustrated in FIG. 1A.
Figure 7B:
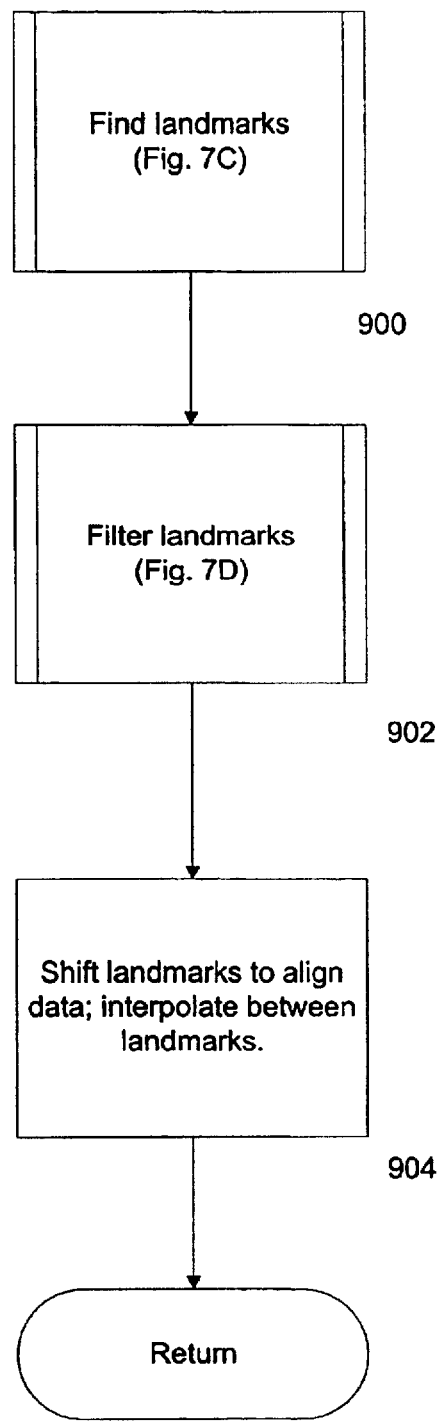
FIG. 7B provides an example of steps that can be used for the "Aligning Spectra Across Conditions" module illustrated in FIG. 1B.
Figure 7C:
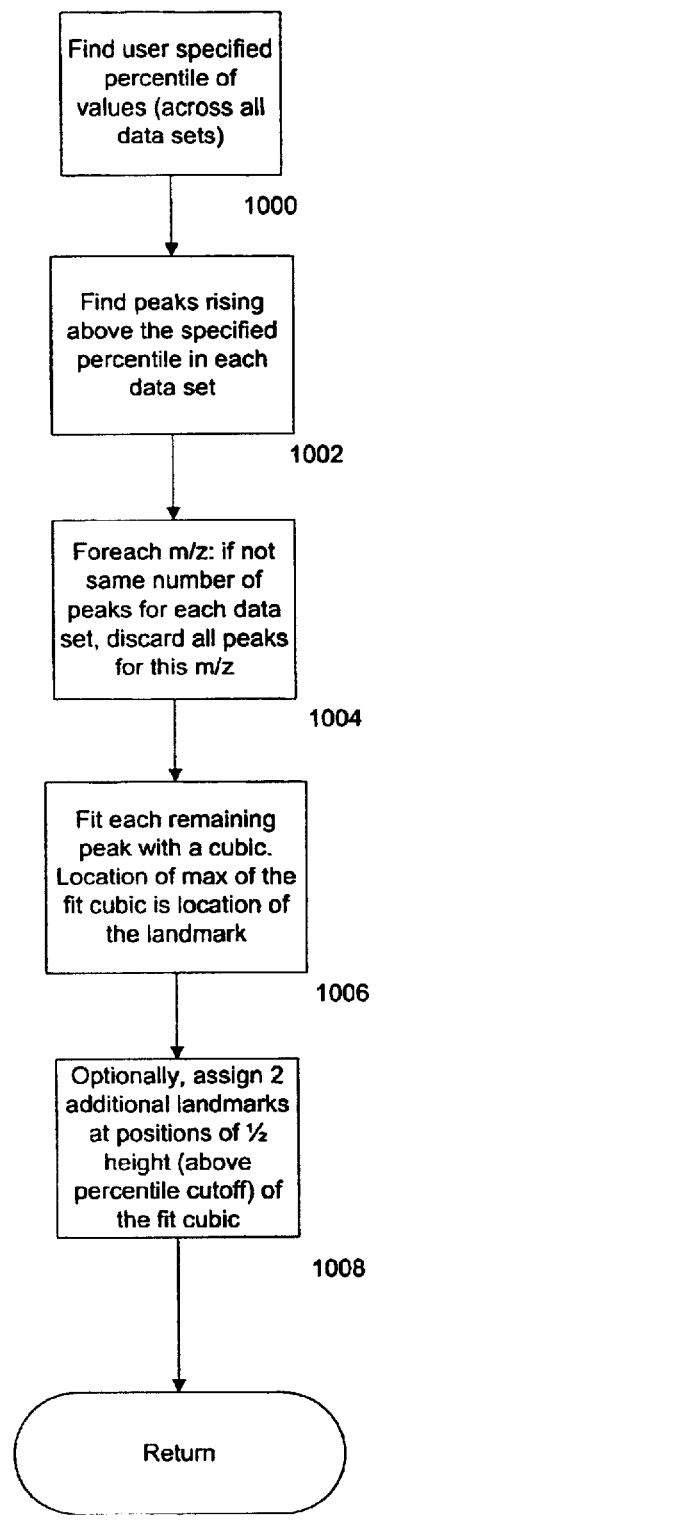
FIG. 7C provides an example of steps that can be used for the "Finding Landmarks" module illustrated in FIG. 7B.
Figure 7D:
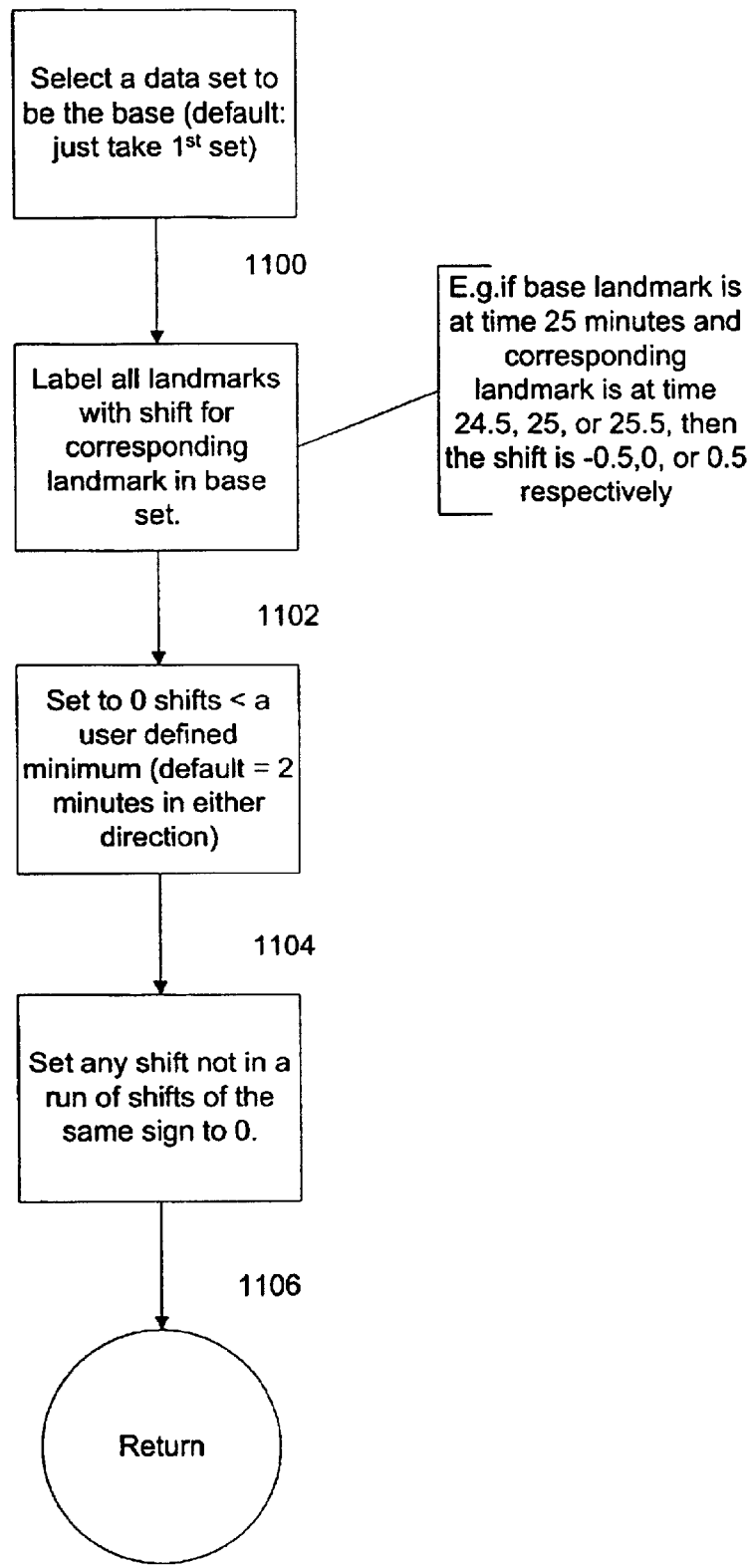
FIG. 7D provides an example of steps that can be used for the "Filtering Landmarks" module illustrated in FIG. 7B.
Figure 8:
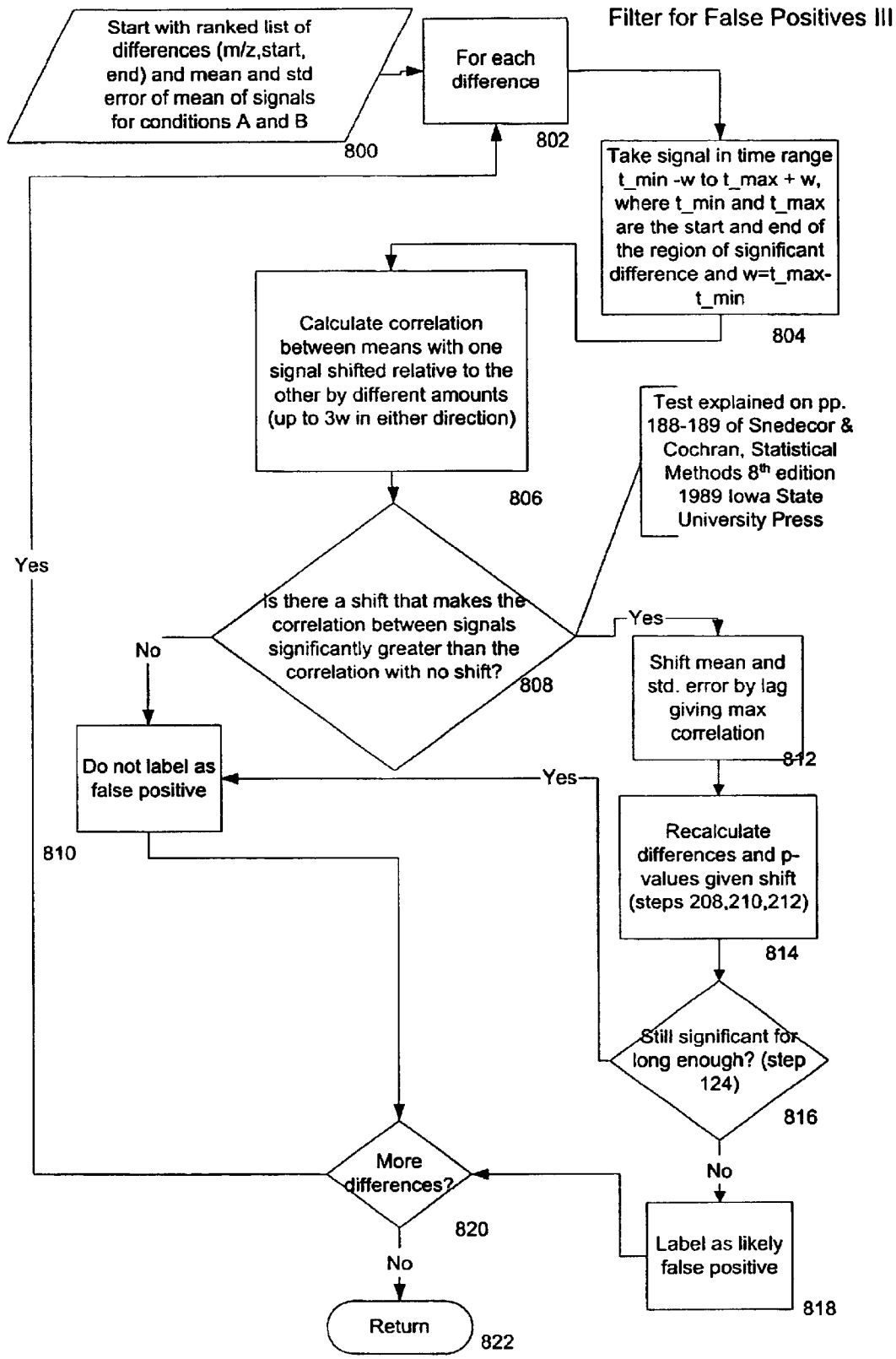
FIG. 8 provides an example of steps that can be used as an alternative method of filtering for false positives.

An example of different embodiments for identifying analytes differing in abundance between sample sets is schematically illustrated by flow charts provided in FIGS. 1–8. FIGS. 1A and 1B illustrate steps for an overall process. FIG. 2 provides an example of steps that can be used for "Finding Differences". FIG. 3 provides an example of steps that can be used for "Group Results". FIG. 4 provides an example of steps that can be used for "Filtering for False Positives I". FIG. 5 provides an example of steps for "Filtering for False Positives II". FIG. 6 provides an example of steps that can be used for the "Output and iteration module". FIG. 7A provides an example of steps that can be used for the "Aligning Spectra Within Conditions" module. FIGS. 7B, 7C, and 7D provide steps that can be used for the "Aligning Spectra across Conditions" module with the "Finding Landmarks" and "Filtering Landmarks" submodules. FIG. 8 provides an example of steps that can be used as an alternative method of filtering for false positives.

The embodiments illustrated in the present section and FIGS. 1–8 for the most part employ m/z related data containing a time index. Based on the disclosure provided herein numerous variations are possible including variations not containing a time index, variations containing a time index and one or more additional indices, and variations containing one or more indices none of which is a time index.

A. Gridding the Data (Also Known as "Binning")

Data analysis is facilitated by binning together data having related m/z values and/or indices. "Related" can mean similar in value or related through other relationships such as synthetic or catabolic pathway, pathway regulation, or attributes relating to experimental factors. Binning is useful in facilitating direct comparison between data sets. Repeated analyte measurements or analyte measurements made on different samples in one or more sample sets will not necessarily occur at exactly the same index variable or measure exactly the same m/z ratio, which can complicate direct comparison.

Binning can be illustrated by using intensity data, time, and m/z data generated with liquid chromatography-mass spectrometry ("LC-MS"). Analogous techniques can be employed with other (or no) index variables.

Using LC-MS, the m/z and time measurements can be rounded to user-specified levels. In different embodiments measurements are rounded off to the nearest unit or to about 0.5 for m/z and to about 0.05 or about 0.025 minutes for time. The set of resulting m/z identifiers is the set of "bins." Rounding is one way to create a many-to-one relationship between m/z data and m/z identifiers.

The fineness or coarseness of the binning can be set in advance, for example, based on the opinion of a mass spectrometrist, knowledge of the operating characteristics of the mass spectrometer being used, or set by visually examining chromatograms or spectra before or after the experiment. If more than one signal from a set ends up at the same grid point they are summed to give total signal at that grid point.

Uniform gridding is not required. The width of a bin could depend on time, other index variables, or m/z. Non-uniform gridding might be useful, for example, in compensating for non-uniform diffusional effects (e.g., time bins increase in width with time) or non-uniform mass precision (e.g., m/z bins increase in width with m/z). One method for performing non-uniform binning is to transform the index-variable or m/z before binning. If, for example, a logarithmic transformation is used on m/z with uniform bin widths in the transformed space, then each bin would correspond to the typical precision of an m/z measurement, which is proportional to m/z. Non-uniform binning can be performed using m/z identifiers non-uniformly spaced throughout their range, for example, logarithmically or geometrically spaced or spaced in a manner dependent on the signals in a bin.

As an alternative to, prior to, or simultaneous to binning, the available signals can be filtered. In linear filtering, the signals are convolved with an arbitrary (but generally decreasing with time and m/z) kernel in the time direction alone, in the m/z direction alone, or a two-dimensional kernel in time and m/z. A 1- or 2-dimensional kernel could be symmetric or have any asymmetries. An up-to-n-dimensional kernel can be employed with n−1 indexing variables (in addition to m/z).

Additional examples of filtering include non-linear filtering such as with quadratic or higher order operators such as those used in blind deconvolution of instrument point-spread functions. (Juang et al., IEEE Trans. Acoust., Speech, Signal Processing, vol. ASSP35, pp. 947–954, 1987; Gillespie et al., IEEE TRANSACTIONS ON SIGNAL PROCESSING, 49:485, 2001; J. Pitton et al., *IEEE Transactions on Signal Processing* 43:1996–1998, 1995; Fang et al., *IEEE Transactions on Signal Processing* 43:2582–94, 1995.) Both linear and non-linear filtering can be performed on original or transformed m/z and/or index variables. An example would be to use a fixed-width Hamming window on logarithmically transformed m/z to smoothly capture precision-based signal distributions. The use of such transformations and linear or non-linear filters would have to be compensated for by normalizations and/or computed and/or measured calibration curves for the purposes of subsequent analysis measuring relative quantities of the analytes in the two conditions.

Different m/z values (either measured data or identifiers) can also be combined either randomly (as part of a stochastic search technique) or for combining m/z values with relationships that are believed a priori. Examples of such relationships include isotopes, co- or post-translation modification of proteins or peptides, methylation of DNA, and/or metabolic or other pathway relationships. The (possibly linearly or nonlinearly weighted) contributions of these m/z's would then be joined as a single statistic and treated as a single m/z identifier. Such "combined" m/z identifiers could be treated as a separate dimension in the data (with units of m/z and treated as such). Thus, the analysis on such combined m/z values (and corresponding "combined analytes") could be performed either in addition to or in parallel with the analysis of m/z values processed in other ways.

B. Alignment

Spectra generated from different samples, or different spectra generated from a single sample, can be aligned to take into account variability between the samples. For example, there may be substantial variability in repeated LC-MS spectra. Some variability may be introduced during the experiment. One possible source of such variability is changes in elution time, possibly caused by changes in flow or chromatographic media or differences in sample composition.

B.1 Systematic Shift

If there is a systematic shift in elution times between the two samples, the corresponding time coordinates of the signals should be adjusted to correct for the shift. A systematic shift can be corrected, for example, based on the assumption that most components of two samples will be similar, so that maximum correlation between the signals will come when the elution times are properly aligned between the two sets of spectra.

An example of a procedure correcting for systematic shift between sets of spectra involves:

1) Measuring the correlation between the means (over spectra sets) of signals with no shift and at a small set of positive and negative time shifts; calculate shifts up to, for example 10 time steps in each direction, and use a suitable p-value (e.g., 0.75) to define significance. Choices for these parameters could be based on knowledge of the precision of the index variable in question, and might be informed by doing like vs. like comparisons. To speed computation of these correlations, and to avoid excessive influence of extremely large values, one could consider only times and masses for which the signals are between the 90th and 95th percentile of all m/z-intensity pairs for both spectra sets. The 90 and 95 lower and upper bounds are user-definable parameters.

2) Checking whether each correlation is significantly greater than the correlation with no shift; and 3a) If no shifted correlation is significantly greater than the unshifted correlation, then proceed without shifting the two conditions relative to each other, otherwise 3b) Choose the shift that gives greatest significantly higher correlation.

An alignment correcting for shift in elution time might have little benefit in light of, for example, a measured high false positive rate determined for a particular data set as determined by the procedures outlined Section II. I. "Sensitivity and Specificity" infra.

Another method of correcting for shifts in elution time involves examining identified differences to identify those that seem to arise from shifts in elution time, measuring the apparent time shifts, and correcting for them in a second round of analyses. An example of techniques for re-alignment is described in Section II. H. "Re-Alignment" infra.

B.2. Aligning Using Landmarks

An additional method of detecting and correcting for shifts in elution time, either systematic shifts between spectra arising from two samples, or shifts among multiple spectra arising from a single sample, involves aligning "landmark" features in the data sets. Landmarks can be created by spiking into the samples a particular substance or substances with known attributes, such that the substances can be expected to give easily detectable signals at known mass-to-charge ratios at (approximately) known "expected" values of index variables, such as elution times. Landmarks can also be found by examining the data sets to find appropriate features, as described below. Given the landmarks, different spectra could be aligned by linearly or non-linearly or piece-wise polynomially transforming the index variables for each spectrum so that the landmarks line up.

Spiked-in Landmarks

If landmarks are created by spiking substances into the samples, those substances should have appropriate attributes. One highly desirable appropriate attribute is that the expected values of all index variables of landmark signals resulting from the spikes should be distributed across the range of observed values for each index variable. Other appropriate attributes would for example comprise having a low probability of reacting with or otherwise interfering with detection of analytes of interest, being easily and economically obtainable, and being detectable at low levels. Expected signals from naturally occurring reactions of reagents used in sample preparation could also be used, such as self-digestion products of trypsin or other enzymes.

Finding Landmarks Without Spiking

If landmarks are based on features found in the data sets, the features could be, for example, peaks with amplitude larger than a fixed percentile of observed peak amplitudes. A "peak" here is a local maximum and its surrounding region (for example in m/z identifier dimension and time) as defined using algorithms for chromatographic peak identification.

For example, a "peak" could be defined as a contiguous (in index variables) set of intensities larger than a fixed percentile of observed intensities, or larger than a fixed fraction of the maximum observed intensity. The intensities could be required to remain above the threshold for a sufficiently large set of index variables (for example, for at least 8 seconds, or some other user-specified length of time, if the index variable is time). Each selected feature will appear, ideally, in each individual data set, or in as large a fraction of the data sets as possible.

If a particular landmark is missing from a spectrum, it can be imputed with a measure of central tendency of the position (in index space) and amplitude (in intensity) over the other spectra for which that landmark exists. For some of the methods defined below, missing landmarks could just be skipped and would not require this imputation.

If landmarks are based on features found in the data set, it is desirable that the selected features be distributed across the range of each index variable used in the experiment. This can be accomplished in several ways. One way is to find features in the full data set and then select features giving a desirable distribution of values for each index variable. Another way is to divide the data set into subsets, each encompassing a range of the values of each index variable, find features giving a desirable distribution of values of each index variable within each subset, and combine the sets of features. Overlapping ranges of index variables might be used so as not to miss useful features at or near the boundaries of the ranges of index variables.

Ranges of index variables defining the subsets could be determined in different ways, for example by dividing the observed range of each index variable evenly into a particular number of subsets, or in a data-dependent way by requiring that a given percentage of the total number of peaks (as defined above), or a given percentage of the total number of features, or a given percentage of the total signal be included in a given range (where total means integrated over m/z and/or index variables).

Grouping Related Landmarks

It might be effective to reduce the set of landmarks by combining information from multiple peaks appearing to arise from different isotopes and/or charge states of a single analyte. Such "multi-peak" groups could be identified as described in Section F "Re-sorting," infra. Such groups might be represented by a single peak or (m/z-identifier, index) pair with index value based on the peak in the group with the maximum signal, the average index value of the peaks in the group, or a signal-weighted average of the index values of the peaks in the group. Each group would then be considered a single landmark. Such a landmark could be given extra weight in calculating realignment, for example by summing the intensities of the constituent peaks (if amplitude is being used to help select or use landmarks).

Reconciling Information From Multiple Landmarks

It is possible that multiple landmarks may be found in a single range of index variables. For clarity and without loss of generality, this discussion will use elution time as an example. If multiple landmarks are found in a particular time range (after grouping as described above), it is possible that they will give varying estimates of appropriate shifts. One landmark might, for example, suggest a shift, relative to a reference time, of 4 seconds, while a nearby landmark suggests a shift of only 1 second, or no shift at all. The definition of the reference time (that is, to what the spectrum is being aligned) is discussed below.

Given a set of landmark times and associated shifts piecewise linear, piecewise polynomial, spline, and similar interpolation methods well known in the art can be used to obtain a single smooth shift function which maps time in one spectrum to a reference time. This interpolation process can, optionally, use landmark characteristics such as m/z-identifier, amplitude, and/or duration to weight their contribution to the summary function.

A certain amount of variability in elution times and assigned peak times is inevitable due to both physical variability in elution time and variability in intensity. Shifts in elution time smaller than a user-specified threshold could be ignored, with the threshold based, for example, on user estimates of the expected variability. In an extreme case, the order of two landmarks close to one another might be reversed in different spectra, making it impossible to find a single order-preserving transformation that will map all landmarks to their counterparts. This could indicate that either the threshold used was lower than the actual variability, or that there is an unanticipated problem with the data being analyzed. In such a case, the user should probably be notified that such a conflict has arisen.

What to Align to: Individual Spectra and Synthetic Representatives

Spectra may be aligned to one another, or to some other standard. Alignments could be performed pairwise between successive pairs of samples iteratively. For example if a spectra set has N samples J is aligned to 2, 2 to 3, ... N−1 to N, N to 1, ... until a stopping criterion is reached. That stopping criterion could be, for example, a fixed number of iterations through all the samples in a spectra set, or a degree of convergence of the warping such as less than a fixed percentage change in warping parameters between the $k^{th}$ and $k+1^{st}$ iterations.

Alternatively, all spectra could be aligned to a single representative. For example, the representative could be the single spectrum with the most landmarks in common with other spectra, or, one that has the smallest distance to all the other spectra. To calculate the distance between a selected spectrum and the other spectra, calculate the distance (in index-variable space) between each landmark in the selected spectrum and the corresponding landmark in each of the other spectra. The distance is a measure of central tendency of this set of between-landmark distances.

Alternately, the spectra could be aligned to a synthetic representative composite made from appropriate data in the various spectra. For example, it might be desirable to use a synthetic representative if parts of various spectra provided especially noisy or unreliable data due to problems in an experiment.

A synthetic representative could also be constructed from modified spectra. Modifications could include non-linear transformations such as setting to 0 values meeting some criteria (for example, values in the original data farther than some user-selected distance from a peak, or larger or smaller than either a fixed or data-dependent threshold, might be set to zero).

Applying Alignment

Application of the warping (alignment) function could be performed on the original data or on the binned data. If performed on the original data, the resulting warped data would have to be binned again. If performed on the binned data, the results would have to be redistributed among the bins. This redistribution could be performed by putting all of a signal into the bin closest to its computed bin number. For example, if bin 35 is mapped to bin 32.3, then the signal in bin 35 could be put into bin 32, and similarly for the signal of all other bins which also mapped to the interval $31.5 \leq$ mapped bin number $\leq 32.5$.

Alternatively, the signals could be redistributed using any smoothing method to reduce the potentially artifactual discontinuities in the spectra resulting from small shifts in computed bin number causing changes in discretized bin number, creating significant shifts in intensity distribution. One such method would be to linearly distribute signals over neighboring bins. Here if bin 35 is mapped to 32.3 then 30% of the signal would be put into bin 33, and 70% into bin 32. In general a signal mapped to bin b>0 would have (1-frac(b)) of its signal put into bin floor(b), and frac(b) of its signal put into bin ceil(b).

Alignment Between Spectra Set

In addition to or instead of performing alignment within a spectra set, it can also be advantageous to perform the alignment between spectra sets. This could be performed using a procedure for aligning a single spectra set but by including examples from all spectra sets to be compared as though they were in the same spectra set. This technique might be best used when the spectra sets are generated from samples that are expected to have a significantly larger number of similarities than differences.

Alignment between spectra sets could also be done by optionally performing the alignment on each spectra set separately, then aligning the aligned spectra sets to each other. The latter alignment could be performed by generating a representative spectrum from each spectra set, finding the appropriate alignment between these representatives, and then using the resulting alignment function (or alignment functions if there is more than one pair of spectra sets under consideration) to align all of the spectra in the spectra sets under consideration. The representative spectrum could either be an unaltered spectrum from one of the spectrum sets, or a computed combination of the spectra in a spectrum set. Examples of combinations that could be used for this purpose are described above in terms of how to align spectra within a spectrum set. A representative could be computed using either the binned or unbinned data.

Alignment on Variables Other Than Time

Analogous alignment or re-alignment methods may be performed on indexing variables other than time or on m/z, with the latter being potentially useful to better calibrate between runs or between instruments or for MALDI, SELDI, or profile data.

An Embodiment of Within-Spectra Set, Landmark-Based Alignment.

In one embodiment, alignment of spectra within a single spectrum set is performed as follows. First, divide the total time (or other index) range into overlapping or non-overlapping sections. In each time section, for each m/z identifier, in each data set, look for peaks in the intensity signals by finding sufficiently long runs (for example, extending over at least 8 seconds, or some other possibly amplitude-dependent user-chosen length) of intensities larger than some selected quantile of the intensities (for example, the 95th percentile, or a fraction of a percentile).

To prevent ambiguities, for each data set select only those m/z identifiers with only a single peak in the time section currently under consideration (at the users option, identifiers with multiple peaks in the current time section could also be used). Next determine which m/z identifiers have selected peaks in all of the spectra in the spectrum set in consideration (or in the largest possible number of spectra if not found in all). Among those peaks, choose the ones with desirable properties determined by the user. For example, peaks can be chosen with the highest intensities, to minimize the likelihood that they arose by chance, or peaks with the most consistent intensity across spectra, or peaks that appear in combination with other peaks that appear to be related either as isotopic peaks or different charge states from a single precursor, or peaks with the most consistent times, or peaks with the smallest variability in time across spectra, or peaks with the largest variability in time across spectra) that also cover the time section as evenly as possible, possibly as determined by some user-specified minimum distance between each pair of selected identifiers. This process has defined a set of "landmark peaks" with corresponding m/z identifiers.

Now choose as the "base" spectrum one with selected m/z identifiers (and corresponding peaks) that match the largest possible number of m/z identifiers (and corresponding peaks) in the other spectra for this spectrum set. Align each spectrum to the base spectrum by performing piecewise linear interpolation of the index values between landmarks. After differences have been identified between two aligned spectra sets each of which has been aligned using the procedures just described, the interpolating functions can by methods well known in the art be used to determine the time in each (unaligned) individual data set at which the original signals can be found. The choice of landmark peaks above based on uniqueness within an m/z and time range makes it extremely unlikely that landmarks from two different spectra will not be properly identified as corresponding to each other when they should, or to correspond to each other when they should not.

EXAMPLES OF ADDITIONAL EMBODIMENTS

Examples of additional embodiments involving landmarks include the following:

1) signals in a set of spectra are aligned by aligning one or more landmarks, where each of the landmarks is a peak at a particular m/z identifier and at a particular set of values of index variables;
2) at least one landmark is found in each of the spectra or in each of a substantial majority of the spectra;
3) the landmarks are found in the data by identifying peaks that occur in all spectra in a spectra set at the same m/z identifier and at nearly the same set of index variables, and using as the landmarks the set of index variable values at which the largest intensity values occur;
4) landmarks are found in the data by identifying peaks that occur in all spectra in a spectra set at the same m/z identifier and at nearly the same set of index variables, smoothing the intensities as a function of index variables, and using as the landmarks the set of index variable values at which the largest smoothed intensity values occur; and
5) the spectra are aligned by shifting the set of index variable values associated with each of the landmarks to the set of index variables values associated with the landmark in some reference spectrum, and intermediate index values are assigned by interpolation (e.g., linear or polynomial). The reference spectrum can be, for example, (a) a randomly chosen member of the set of spectra or (b) a spectrum that has lowest central tendency of distance to all other spectra in the set of spectra, wherein distance is Euclidean or Mahalanobis or Manhattan distance between corresponding landmarks.

B.3. Alignment Using Summaries of the Data over m/z

Spectra can be aligned using some representative of the data depending only on index variables and not on m/z identifiers. The representative could be, for example, the mean or median or mean of a percentile range or other point statistic calculated at each (optionally binned) time or other set of index variables across the spectra in a spectrum set. One example would be the mean of the base peak chromatograms of the spectra or the base peak chromatogram of the mean of the spectra. The notion of base peak chromatogram could further be generalized to include, for each fixed time bin or bins, a given percentile or mean of all signals in a percentile range in place of the maximum signal at a given time (as usually practiced by those skilled in the art). Also, any m/z-identifier-independent summary of the landmark data described above could be used as a representative. These representatives can then be aligned using dynamic time warping as described in Section II. H. "Re-Alignment" infra.

C. Normalization

Another possible source of variability between spectra is that different putatively identical samples may in fact include slightly different amounts or concentrations of various analytes. Further, even with the same sample, many factors can influence the efficiency of the process from sample loading to sample introduction in to the mass spectrometer. Such possibilities can be dealt with by normalizing the data.

Normalization can be performed by dividing the signals by a factor calculated using the spectra to be normalized or a set of spectra to be normalized as a unit due to some commonality in the experimental process. In general the normalizing factor could be a non-linear, possibly vector-valued function of the signals in the quantile range of interest, such as logarithm, polynomial, square root, and rank. The normalized values could be any function of the m/z-intensity pairs and the normalizing factor, where the specification of that function could depend upon the values of the normalizing factor.

For example, in an embodiment, for each combination of index variable values, the normalizing factor is the mean of all m/z-intensity pairs between the $90^{th}$ and $95^{th}$ percentiles of the distribution of m/z-intensity pairs (these quantiles can be set by the user). In this example, the top five percent of signals are not included because this prevents a few very high values from dominating the normalization. Changing the lower limit of included signals from the $90^{th}$ to the $75^{th}$ percentile does not appear to substantially affect the normalization. Other ranges chosen by absolute range, other percentile ranges, or other statistical range definitions (based on a priori distributions) could be used. These ranges could also be used in conjunction with summary factors other than the mean, such as median, mode or geometric mean. In the case where there are no index variables or there is only one combination of index variable values normalization cannot be performed this way.

In an embodiment using data without any index variables, we can assign each m/z-intensity pair an identical arbitrary set of index values and proceed as above. For example, in a MALDI experiment (in which there is no time index), the normalizing constant might be the mean of all intensities at all m/z values, or the mean of all intensities between certain percentile points of the distribution of intensities.

D. Evaluating Differences

The significance of changes between spectra sets in an m/z-intensity pair, in light of signal variability within spectra sets, can be determined, for example, using standard statistical techniques. A wide range of statistical techniques (both parametric and nonparametric) can be used to estimate the significance of difference in m/z-intensity pairs. Significance is expressed as a monotonic function of p-value. A p-value represents the likelihood that an observed change between spectra sets in the distribution of intensities associated with a particular m/z identifier could have arisen by chance in the absence of differences between the sample sets in the level of some analyte. Ranks that come from statistical measures of the ability to correctly classify samples can also be used in combination with or in place of p-values.

Parametric methods can be used to calculate p-values. A wide range of different parametric methods are well known in the art. (Snedecor & Cochran, Statistical Methods, $8^{th}$ edition, 1989, Iowa State University Press; Kanji, 100 Statistical Tests, 1999, SAGE Publications). Examples of such methods include t-test and analogous tests not assuming Gaussian (or "normal") distributions of the data. For multiple conditions (more than two conditions) Analysis of Variance could be used for each identifier.

The use of the t-test to measure significance is illustrated in Section X. "Example 1" and "Example 2" infra. Example 2 analyzes LC-MS spectra generated with a time index. At each time and m/z, there are n1 signals from condition 1 and n2 signals from condition 2 where at least one of n1, n2 is greater than one or there is ancillary variability information based on other data sufficiently similar to those being taken. At each time and m/z the significance of the difference in the mean signals given the observed or assumed variability was determined. Because spectra in this example have signals that are more nearly log-normally than normally distributed, additional computations were performed to determine the mean and variance of the corresponding normal distribution of logarithms, and the rest of the analysis was performed on both sets of p-values. In such cases results obtained using the imputed normal distribution of logarithms may be preferred to those obtained using the distribution of untransformed values.

If a particular instrument or experimental protocol produces a reproducible relationship between the mean and estimated variance of the sample, then variance can be imputed for a spectra in a sample set. This can be particularly useful if n1 and n2 are small, for example n1=1 or 2 or any integer less than 100 and/or n2=1 or 2 or any integer less than 100. In some of our data sets the relationship variance= mean to the 2.1 power was observed and provided this capability.

It is also possible to get an approximate measure of such a mean-variance relation even if only one signal is available at each m/z value and time. This is done by assuming that signals near one another in time are estimates of similar underlying quantities. In this case, we can take groups of N signals adjacent in time (where the groups may be overlapping or non-overlapping, and N is specified by the user; for example N=5 and N=10), and find the relationship between the means and variances for these groups. In the spectra that have been checked, the relationship determined in this way is virtually identical to the relationship determined using signals obtained from multiple spectra. In some groups the signals may uniformly increase or uniformly decrease, and it may be unreasonable to treat them as repeated measurements of a single quantity (they may form, for example, the rising or falling slope of a peak). Such signals can be excluded from the set used for estimating the relation between mean and variance. In our experience this makes almost no difference in the estimated relation between mean and variance. In general, using such imputation is expected to give worse results than actually using replicates, but might be adequate with sufficiently reproducible experimental protocols.

P-values can also be calculated using the minimum of a number of methods. For example, the analysis described above in which the means and variances of actual signals are used, and the analysis described above in which the means and variance of the implied distribution of logarithms of signals are used, thereby obtaining the union of all points of interest. If this is used, the resulting net p-value should be multiplied by the number of methods used (by the Bonferroni method well known in the art) or statistically corrected in some other way.

A non-parametric method can also be used, for example, to produce a p-value in cases where the assumptions underlying a parametric method are not known to be appropriate. Different non-parametric methods are well known in the art (Kanji, 100 Statistical Tests, 1999, SAGE Publications; W. J. Conover. Practical nonparametric statistics (2nd ed.). New York: John Wiley & Sons, 1980). Many non-parametric tests would also accommodate more than two conditions.

An example of a non-parametric method, involves replacing the difference between mean signal differences with its corresponding percentile in the observed (empirical) distribution, across all times and m/z identifiers, of differences between the mean signal of condition 1 and the mean signal of condition 2. (Mean here is taken across spectra within a sample set.) These percentiles, which range from 0 to 1, can be treated as p-values. This method has the disadvantage that it does not directly take into account the variability of the signals, only the difference between averages. This method implicitly assumes that the variance of all signals is equal. Thus, it can miss small but statistically significant differences in low-abundance analytes.

Robust statistical methods can also be used to produce p values (Wilcox, Introduction to Robust Estimation and Hypothesis Testing, Academic Press 1997). Robust statistical methods are methods that attempt to minimize the influence of extreme data points or other departures from distributional assumptions (thus in some contexts non-parametric tests, which do not depend on distributional assumptions, are considered robust). One example of a robust statistical method is the "trimmed mean", which is a mean calculated after excluding some portion of the largest and smallest measurements. The number of measurements excluded may be specified as an absolute number (for example, the three largest and three smallest measurements) or as a portion of the available data (for example, the largest one percent and smallest one percent of measurements). A trimmed standard deviation can be defined similarly. A t-test performed as above, but using trimmed means and standard deviations (and correspondingly smaller degrees of freedom, because our mean and standard deviation are based on fewer measurements), might be more robust to outliers than a t-test performed without excluding any values. Resampling methods can also be used to compare the trimmed means of two distributions (Wilcox, Introduction to Robust Estimation and Hypothesis Testing, Academic Press 1997), but require much more computation.

Excluding values by trimming has possible disadvantages as well as possible advantages. First, we frequently have small amounts of data, so that excluding some values substantially decreases the power of the test. Second, extreme values may reflect the true variability of an measurement, in which case using trimmed means may increase the number of false positives.

Other robust tests use other robust estimators of central tendency and variability. For example, using median instead of mean and a multiple of the interquartile range instead of standard deviation. A wide range of robust statistical tests are discussed in Wilcox, 1997.

Permutation tests (Phillip Good, Permutation Tests, Springer 1994) can also be used. A permutation test in this context, might, for example, compare the t-statistic (or some other user-specified statistic) at each point (for example, m/z identifier with accompanying index variables) to the set of such statistics at all points. P-value would be assigned by rank within the list of observed values of the statistic.

The statistical analyses above can be performed on any function of the m/z-intensity pairs and/or identifiers and/or index(es). This includes the signals themselves.

E. Time-Persistence

Time persistence of p-values, or equivalent measurements such as pseudo-p-values, can be used to facilitate distinguishing analytes from transient or persistent noise. A matrix of p-values (or equivalent statistics) each corresponding to a particular m/z-intensity pair and time can be determined using techniques such as those exemplified in Section II. D. "Evaluating Differences" supra. For each m/z identifier, p-values for differences between the two sets of experiments lower than a threshold (for example about 0.05 or about 0.1 or about 0.2) and persisting longer than a user-specified minimum time (for example, about 5, about 10 or about 15 seconds, depending on the application) can be identified.

Under a null hypothesis that there is no difference between the two conditions and that all the signals are independent, the likelihood of a persistent signal is the product of the p-values at the constituent time points. Patterns in which at least m of i (user specified) consecutive p-values are below the threshold can be identified. In this case the p-value calculated under independence should be multiplied by (n choose m).

Persistent signals can be ranked by likelihood, with those least likely under the null hypothesis of no significant differences presented first. Signals that persist longer than a user-specified value can, if desired, be considered artifacts and discarded. In different embodiments the user-specified value is at least about 1 minute, at least about 1.5 minutes, or at least about 2 minutes.

Persistence of significance across subsets of an index variable or variables other than time could also be used as a means to further facilitate distinguishing analytes from transient or persistent noise. This could be done instead of, in addition to, in combination with, or independent of considering time persistence. In the case of data having no index values, persistence over a set of m/z-identifiers could be used, including not only isotopic or charge-related subsets of m/z, but also across peaks that are not resolved due to resolution limitations of the data. The latter is demonstrated in Section X. "Example 5-" infra.

F. Re-Sorting.

Significant differences can be sorted into related groups. The existence of related differences in signals can provide additional evidence that each related difference is due to a difference between the level of an analyte in the two sample sets, rather than to noise. Related differences can be grouped together either just for presenting results or for modifying the likelihood of the grouped results.

Sorting can be based on different properties such as the possibility of being isotope signals or the possibility of representing different charge states of a single base analyte or family of base analytes. The results are then divided into groups based on their likelihood of being solely due to remaining shifts in the relative elution time (in the case of LC-MS with a time index) to automatically find the "false positives". Sorting could also consider other factors, such as being part of a common biological pathway, or shifts in other index variables.

For example, a peptide can, during the ionization that is part of LC-MS, acquire one or more charges. Each charge state $z$ (typically $z$ can be 1, 2, 3, or 4, although in some cases it may be a larger integer) gives rise to signals with different m/z identifiers. Thus, different molecules of a single peptide sequence can simultaneously give rise to ions (and therefore signals) at more than one m/z identifier.

If a peptide has base mass B, then the m/z for charge state $z$ is equal to $(B+z)/z$. Thus, from a particular m/z identifier the possible base masses can be calculated as (mass-to-charge * z)−z.

The possible base masses for each signal in a list for a range of likely z values (typically 1, 2, 3, or 4) can be calculated. Signals that overlap in time and could arise from the same base mass, are grouped together (coincidence or near coincidence in other index variables might also be required in some applications, such as multi-dimensional LC). The list of results is re-sorted, with each group receiving the rank of its highest-ranked constituent signal. Thus, less significant signals that are potentially related by mass-to-charge ratio to more significant signals occurring at the same time are moved up the list.

The p-values of the groups can also be modified, for example, assigning each of them the product of their p-values (under the null hypothesis that the signals are random and independent), then represented as a single item (or grouped in other ways). Index variables other than time might be used in the grouping here as in other operations (i.e., alignment in variables other than time might be required for coincidence).

Different signals may also be related if their m/z identifiers indicate that they come from different isotope states. Isotopes of an element have the same number of protons and electrons, but differ in the number of neutrons. One isotope is generally much more common than all others and produces the dominant m/z-intensity pair. For example, some peptides might contain an isotopic form with a molecular weight different by 1 (or a larger integer n if more than one extra neutron is present) from the molecular weight of the common form. The m/z identifier will be shifted by $1/z$ (or m/z) from the dominant m/z identifier for any charge state z.

The appearance of isotopic peaks or multiple charge states provides additional support for a detected signal. Signals with an m/z identifier that could represent isotopic peaks or multiple charge states, and, if index variables such as time are present, that overlap in index variables, can be grouped together. Also, the shape (as a function of time and/or other index variable or variables) of peaks of two isotopes (and/or charge states) of the same analyte will in general be much more similar to each other than to other analytes. Thus whether two peaks belong to different isotopes (and/or charge states) of a given analyte can be made more certain by measuring their similarity. Measured similarity (for example, correlation, dot product, or rank correlation) of two peaks can be compared either to a general distribution for that measure of similarity or to the empirical distribution of pairwise peak similarities for a given set of measurements. More complex deconvolution of isotopic (and/or charge state) effects is also possible using standard techniques well known in the art. They could also work well on the short (relative to non-statistically filtered) lists of m/z identifiers in a produced ranked list of differences.

Though more computation might be required to do so, isotope pairing could also be done on mean or individual spectra before the rest of the process described above is completed, and the signals for a given set of isotopes of a putatively single analyte could all be combined through summation or non-linear processes in order to treat them as a single entity. Similar processing can optionally be done to combine signals putatively arising from different charge states of the same analyte (which should also have relatively similar peak shapes, as described above for isotopes) before or after differences are identified.

An additional grouping issue arises when m/z values are represented with high resolution. In this case, a single analyte in a single charge state may give rise to signals at a range of m/z's due to limited precision of the instrument's method of mass analysis; in general, the intensities will rise to a peak near the true m/z value, with weaker signals extending some distance on either side. That is, each true difference gives rise to a small "peak" of apparent differences (or perhaps, if index variables are also included, a "ridge"). The results are easier to interpret if combined into groups, each representing a single analyte with a particular m/z value. Such grouping is similar to the search for time persistence described above in section E, although here the persistence is across m/z values rather than time. Groups can be identified by finding runs of some chosen number of consecutive significant results (for example, 8 in a row or at least m out of n in a row where m and n are integers with m less than or equal to n).

It may also be required that the consecutive m/z's span some minimum width, which may be expressed either in absolute terms (for example, half an m/z unit) or in relative terms, with the latter being in keeping with m/z precision for a typical instrument being proportional to the m/z being measured (for example, the width must be at least one quarter of one percent of the smallest m/z in the group). The grouped results themselves might be further grouped, for example to connect groups that appear to arise from different isotopes and/or charge states of the same precursor. For data with index variables, grouping in the m/z direction might be done either before or after looking for persistence in time or along any other index variable or variables.

In another embodiment grouping is performed using hierarchical or non-hierarchical agglomerative or divisive or other clustering based on weighting of points in a space whose dimensions comprise m/z, and/or signed log likelihood and/or signal for condition A and/or signal for condition B and/or the difference between the signals for conditions A and B. Such clustering methods and heuristics for choosing the dimensional weights are well known in the art.

If other index variables are also present, they can also be used as dimensions for the clustering, allowing grouping to take place over these index variables as well. Further, by also including a dimension of representative m obtained using m/z corrected for putative charge or isotope by multiplying by a putative charge and subtracting the mass of any charge inducing entities (such as protons) and subtracting a putative isotopic mass difference, the clustering can facilitate the grouping of evidence for isotopic and charge-state information for single analytes producing multiple peaks due to isotopic and multiple charge phenomena.

G. Partitioning

Partitioning can be performed to further facilitate identification of "false positives", which are differences due to experimental or computational artifacts rather than due to differences in the levels of analytes. Detected differences can be partitioned into subsets representing an approximation to the probability or likelihood that they are false positives.

One type of false positive arises if two signals slightly shifted in time (or other index variable) give the appearance of a difference. In particular, if two nearly identical peaks are shifted relative to one another (FIG. 10), then both the rising and falling slopes may appear to represent significantly different signals. Where the peaks cross, however, there will typically be at least one time point at which the difference is not significant. Such signals can be flagged for further analysis. In dealing with such signals two cases can be distinguished: (1) when both the rising and falling slopes have been detected as significantly different, and (2) when only one has been detected as significant.

Shifted signals in which both halves are detected as significant ("full shifts") can be identified by examining m/z-intensity pairs with significant differences at more than one time. If two signals at the same m/z identifier are sufficiently close in time (a user-defined parameter), and differ in opposite directions (A greater than B in the earlier signal, and B greater than A in the later one, or the other way around), they are grouped together. These "combined" signals are then re-aligned in time (or other index variables) by maximizing correlation between the two peaks through a grid or binary search or other optimization methods, and re-compared. Measures other than correlation, such as differences in index-variable-parameter from a linear or non-linear fit to portions or the entirety of the curve of interest, rank correlation, the negative of the p-value between the signals, or the negative of the area between curves, can also be used. If the difference is no longer significant, the combined signal is marked as a possible false positive due to shifting. If the difference remains significant, the component signals are deleted from the list, and replaced by the combined signal, with its place determined by its level of significance.

The method just described does not work if either the rising or falling slope has not been detected as significant. All signals not grouped together by the previous analysis can be checked to see whether they meet all three of the following criteria:

(1) Neither of the mean (across spectra within a sample set) signals has a peak in it. Here a peak is defined as a point at which the signal is greater than at any of its nearest N (a user-defined parameter) neighbors on either side. Thus if N=2, a peak is an average signal larger than the average signals at the two immediately preceding and the two immediately following time points (this can also be checked in other index variables);

(2) The slope(s) of the least-squares regression line expressing average signal as a function of time (and/or other index variables) is significantly different from zero for both lines; and (3) The two slopes are sufficiently close to one another, in the sense that the ratio of the larger of the two slopes to the smaller is less than some user-defined threshold, for example, 3.

If all three conditions are met, the signal is flagged as a possible false positive due to time shifting ("half shift"). Full shifts can be partitioned separately from half shifts. Possible false positives can be moved to the end of the ranked list of results and ranked among themselves in order of their apparent significance.

The apparent time shifts ("estimated shifts") for possible false positives can be kept track of for subsequent analysis (see Section II.H. "Re-alignment" infra.). The shift for possible false positives consisting of a rising and falling edge grouped together can be taken as the shift that gives the largest correlation between the re-aligned signals. For possible false positives consisting of only a single rising or falling edge, the shift is, in one embodiment, the difference in x-axis intercepts of the linear regressions relating average signal to time (and/or other index variables). A number of other estimates for index-variable shifts are listed above in the discussion of realigning signals for full shifts.

In another embodiment, it is possible to check whether an apparent difference is due to a shift in time or other index variable(s) between the two spectra sets by checking whether re-aligning the two spectra sets causes the difference to cease to be significant. For example, to determine whether another alignment of the spectra sets might be more appropriate than the actual alignment, one could examine the correlation of the mean intensities between two spectra sets when shifting the second relative to the first by a range of time shifts. Only intensities in some region of the apparent significant difference would be included in the calculation; for example, the region of apparent significance and on either side of that range a region of duration equal to a multiple of 1 or 1.5 or 2 or 2.5 or more times as long as the duration of the region of apparent significance. If no time shift yields significantly higher correlation than exists between the unshifted data sets, then the difference under examination is considered unlikely to be due to a time shift. If some shift does yield significantly higher correlation than exists between the unshifted data sets, then the determination of whether the difference is significant is repeated for the data sets after shifting to yield the highest cross-correlation. If the difference is still significant after shifting, then it is considered not to be due to a time shift. If the difference is no longer significant after shifting, then it is considered likely to be due to a time shift. FIG. 8 shows steps that could be carried out to check for false positives using realignment.

H. Re-Alignment

After estimated time shifts have been flagged, it is possible to use those estimated shifts to re-align the spectra and repeat the analysis. In a realignment step, the various false positive-related categories are used to determine a likely shift.

The median of the distribution of shifts of possible false positives (expressed in the nearest number of bins) can be taken as the best shift (other statistics, such as mean over a percentile range might also be appropriate, and in general any measure of central tendency might be applicable). The re-aligned binned signals can then again be analyzed for differences. In at least one example (shown in Example 2 infra) this technique has reduced the number of partitioned false positives by approximately 80% without affecting the vast majority of the other results. The re-alignment procedure might not be beneficial if the distribution of shifts is too broad or a measure of its central tendency (such as median) is not significantly different from zero.

Alternatively, the original spectra could be re-aligned according to the median (or other statistic) of the distribution of shifts (which need not be expressed in the nearest number of bins), and part or all of the entire process repeated, starting by re-gridding the original data and proceeding through the identification of significant differences and possible false positives.

The entire procedure of (1) analyzing, (2) finding shifts, and (3) re-alignment can be repeating one or more times, and can be run iteratively with each new analysis providing the shifts for the next re-alignment. The iteration might be stopped when a "stopping criterion" is met. The stopping criterion would be met if, for example, a sufficiently small (user-defined) number of possible false positives have been identified, or the number of possible false positives identified failed to significantly (for example by more than 0) decrease after some iteration (the results from the previous iteration would be retained in this circumstance).

In some data sets one re-alignment would be beneficial. There might or might not be cases where more than one re-alignment would be beneficial. In different embodiments the re-alignment procedure is performed 0, 1, at least 2, at least 3, at least 4, at least 5, at least 6, at least 7, at least 8, at least 9, or at least 10 times, or at least until the stopping criterion is met.

The shift can be non-uniform in time (or other index variable), so that later times could, for example, be shifted more (or less) than earlier ones. This might be desirable if, for example, there is a change in a characteristic of the liquid chromatography experiment such as flow velocity or temperature. In this case the shifts from one or more spectra (relative to one or more baseline spectra) are fit to a (smoothing) polynomial or equivalent (such as loess; Modern Applied Statistics with S. Fourth Edition, by W. N. Venables and B. D. Ripley, Springer, 2002), and the time coordinates of the corresponding data are then shifted by the values of the fit curve. In a more extreme case spectra in two or more sets could be aligned by setting their signals to zero outside the false positives used to estimate local shifts, then doing a global dynamic time warping (Applied Functional Data Analysis: Methods and Case Studies by J. O. Ramsay and B. W. Silverman, Springer, 2002; Functional Data Analysis by J. O. Ramsay and B. W. Silverman, 1997) to align the remaining signals and using the resulting warp function to shift the time coordinates of the original or binned data. Shifting and related computations can be performed before or after binning.

I. Sensitivity and Specificity

Sensitivity and specificity can be enhanced by increasing the number of spectra analyzed (see Section I. B. supra.). The number of spectra needed to obtain a desired level of confidence, sensitivity or specificity in the output can be estimated using resampling methods or standard power analysis.

In a standard power analysis, the number of replicates needed for a desired level of sensitivity and/or specificity for a given statistical test (e.g., a t-test) can be estimated. This is called finding the power of a test, and is standard statistical technique. The t-test used in the method to estimate statistical significance requires only the mean and variance of signal and the number of replicates. The power analysis can be performed using the imputed mean and variance of the logarithms of signal. It can also be performed using an assumed variance structure as described above under Section II. D. "Evaluating Differences", but is likely to give worse performance in exchange for the possibility of being able to do it before collecting all data.

A resampling method can be used to determine the number of spectra required to detect signals with particular attributes such as strength, amplitude, p-value, and time persistence. This assumes that the data used for this analysis properly represent the statistics of data for which the number of required spectra or samples is being estimated.

For example, data sets containing two or more conditions can be generated by resampling as follows (illustrated here in the case having two conditions). Assume there are N spectra for each of the conditions. For each n from 2 to N−1, there are (N choose n) subsets with n of the spectra, and so there are (N choose n) squared pairs of subsets. For each value of n, the analysis can be performed on M=Min(100, (N choose n) squared) of these subsets. (Here the user-selectable parameter 100 was chosen as a minimum for statistical purposes but can be larger or smaller.) The results can be examined to determine the minimum number of spectra necessary, for example, to achieve the desired probability of detecting signals with given attributes.

Specificity can be measured by examining differences between two sets of spectra taken from the same sample set. There should be no true differences of interest between the sets of spectra, so any signals found can be considered false positives. Such false positives may arise either as statistical flukes or from contamination during sample handling. Having a distribution of false positives with undesirable properties can be indicative of poor data quality.

Thus users could be informed of the number of false positives, the distribution of their p-values (as through a box or "whisker" plot), the distribution of their index values and/or m/z-identifiers (as through a box or "whisker" plot). Any parameters of these distributions such as total number, mean, median, interquartile range, max, and or min, range could be compared to thresholds individually or as weighted sums in order to determine if a data set should be flagged for possibly having quality problems. Such warnings could also be issued based on poor signal to noise ratio in too many of the spectra, where "too many" is any number larger than a user-specified threshold.

Techniques for determining signal to noise are well known in the art. Signal to noise could be determined by, for example, ratios of means over specified percentile ranges such as mean of signals in the $95^{th}$–$97^{th}$ percentile range divided by mean of signals in the $85^{th}$–$93^{rd}$ percentile range. They could also be measured using central tendency of intensities of local maxima divided by central tendencies of all signals. Here a local maximum is a defined over m/z or over an index variable or over any combination of m/z and index variables and can be defined using any technique well known in the art such as requiring a point to be higher than at least n neighbors, for some integer n, with a neighbor being a point with consecutively higher or lower values of m/z and or the index variable or variables, and the values could be as measured or binned.

A resampling method can also be used to measure specificity. For N spectra from a single sample set (where N is greater than three), a comparison can be made between two subsets of spectra with one of them having 2, 3, . . . , or up to floor((N−1)/2) spectra and the other having all the remaining spectra (possibly save 1, so sample sizes are equal for convenience, if N is odd). In a single comparison, two sets of spectra are chosen (without repetition) from the N spectra available, and the analysis performed to find any apparent differences.

Typically, many comparisons will be performed on randomly chosen subset pairs. There are typically many distinct subset pairs, and many ways to choose two subsets of spectra. For example, 100 subset pairs are randomly chosen and compared for each subset size. The parameter 100 can be decreased or increased.

The resulting lists of differences are summarized statistically to estimate the false positive rate. It can be beneficial to examine the distribution across the subset pairs of the number of apparent false positives. Total false positives, and false positive rate can be estimated from this distribution. Further, any differences showing up with sufficient frequency can be examined to determine whether they reflect contaminants differing from one sample to the other (differences that appear on visual inspection of the spectra to be real, yet are not related to the intentionally varied experimental conditions). The distribution of p-values found for these within-sample-set differences could also be used to guide which between-sample-set differences might be of interest.

All of steps in Section II parts (A) through (I) can be performed on a digital computer, and the number of computations performed in any of them other than grouping related differences increases no more than linear times log linearly in the number of m/z identifiers. The number of computations performed in the grouping of related differences increases no more than quadratically in the number of significant differences found between the conditions.

III. Significance of Differences

A "significant" difference is one that is unlikely under some particular set of assumptions about the m/z-intensity pairs in the spectra from the two sample sets. The set of assumptions is called the "null hypothesis", and might typically be that there is no consistent difference in the level of any analyte between the two sample sets, and so no consistent differences between m/z-intensity pairs.

In standard statistical practice the "p-value" expresses how likely or unlikely a particular observed result is under the null hypothesis. The p-value frequently is defined as the probability that the given result would occur given that the null hypothesis is true. Small p-values indicate outcomes that are less likely under the null hypothesis, and therefore considered more significant, that is, better evidence that the null hypothesis is false and there is a real difference between the sample sets.

Typically, a particular p-value is chosen as the threshold for significance in a particular analysis. As in any statistical procedure, some random fluctuations may appear significant even when there is no corresponding difference between the sample sets. In addition, some statistically significant differences might not be of interest in a particular application even if they are not due to or seem not to be due to random noise. In different embodiments the p-value for significance has a threshold of about 0.2, about 0.1, about 0.05, or about 0.01.

In any of the analyses herein, a p-value can be calculated in a number of different ways. In some cases it can be advantageous (in terms of sensitivity and or specificity) to calculate the p-value of an entity (signal difference at a point or in a region of index-variable and/or m/z values) using multiple methods and combining these p-values into a single estimated "final p-value." For example the final p-value could be estimated as the maximum or the minimum or the mean or the median of the p-values determined for that entity. It could also (using a type of Bonferroni correction well-known in the art) be estimated by multiplying that minimum by the number of p-values being considered for that entity. This final p-value is then used when comparing to a threshold. If the minimum method is used to get the final p-value, then the resulting list of significant entities would be a union of the lists that would be obtained from using each of the individual p-value methods independently.

Also in any of the analyses herein, the method of calculating p-values can be approximately calibrated. To perform this calibration a stochastic simulation based on resampling is performed. This and other methods for calibrating p-values are discussed in the context of robust statistical methods in Section D. Evaluating Differences, supra.

IV. Determination of Relative Amounts

Figure 9:
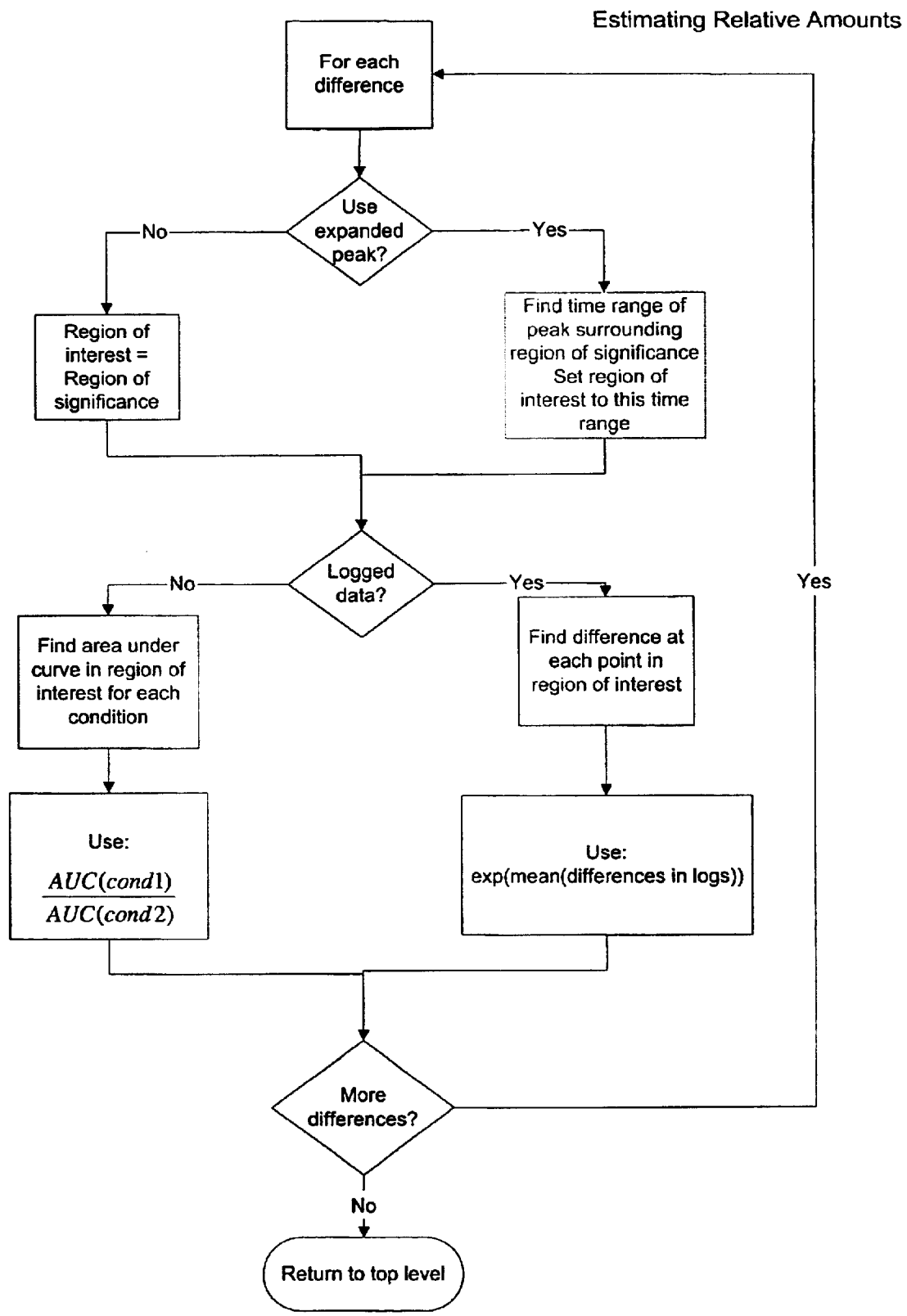
FIG. 9 provides an example of steps that can be used to quantify the relative intensity of signals in two spectra sets.

It is sometimes useful to estimate the amount by which the abundance of detected analytes has changed. A similar measure of "fold change" is commonly used in the interpretation of gene expression data. The information collected by the methods described herein can be used to make such an estimate. FIG. 9 provides an example of steps that can be used to quantify the relative intensity of signals in two spectra.

An estimate of fold-change in analyte abundance can be based on the representations used by the difference-finding algorithm. It can be based on the intensity measurements themselves, or, because of the evidence that the intensity measurements may be approximately log-normally distributed, on the underlying distribution of logarithms.

If the fold-change estimate is based on the intensities themselves, then the change (e.g., difference, relative, or ratiometric) in total area under the intensity curve can be estimated. Such a change could be based, for example, only on the region (in time, m/z, and/or other index variables) in which a significant difference is detected. It could also be based on a region, either narrower or wider than that region, around the region in which a significant difference is detected, such as by starting with this region and finding the smallest region including this region which in the intensity curve includes a local maximum and is bounded by local minima as might be found using common peak finding algorithms that are well known in the art. The intensity curve could be based on any measure of central tendency of intensity across samples in a sample set, including, for example, mean or median intensity at each time point. The fold change could be determined as the mean of measured intensities in one condition divided by the mean of measured intensities in another condition. If necessary, baseline intensity can be estimated and subtracted from the areas (mean being equal to area over time duration) before fold change is estimated.

If the fold-change estimate is based on log intensities, then the difference in area under the curve provides an estimate of the log change. Therefore exponentiating the difference in area under the curve provides an estimate of the fold change. Alternatively, the mean of the exponentiated difference at each time can be used as an estimate of the overall fold change, but using the exponentiation of the mean allows us to average out instability of measurements before exponentiating.

Other enhancements might include subtracting some base signal from each of the measured signals and using the remaining signals to calculate the fold change, or comparing the signals in a region slightly wider (with respect to elution time or other index variable) than the region of significance (to account for the possibility that both signals rise above baseline, possibly by different amounts, before the difference between them becomes significant).

Methods for determining peak areas and baseline are commonly used in interpretation of chromatographic signals and DNA-base-calling, and are well known in the art. Signals could also be compared on a contracted region to be more robust with respect to fluctuations in signal strength near the boundaries. For all such comparisons there could be one region for each spectrum set or a different one for each spectrum. Computations for fold change can be made using warped or unwarped indices or both.

In addition to using statistics measuring central tendency, we can make use of multiple measurements of the relative amounts to get better estimates and/or error bounds for the ratios. For example, error bounds for the fold change estimates could be obtained by resampling. For example, one might choose a subset (containing some fixed portion of the available spectra) of each spectra set, and perform the computations above to estimate the fold change using that pair of subsets. By repeatedly choosing such subsets, a large number of fold-change estimates could be obtained.

The distribution of fold-change estimates could be used to obtain a resampling estimate of the fold change. Any measure of central tendency, possibly corrected for resampling using standard bootstrap techniques well known in the art, could be used the overall estimate of fold change. The distribution of estimates could also be used to determine error bounds, using, for example, the standard deviation of the distribution or percentile points (for example, using the $2.5^{th}$ percentile as the lower bound and the $97.5^{th}$ percentile as the upper bound would give a 95% confidence interval).

In addition to resampling, multiple isotope and/or multiple charge (z) states of a single analyte could be used to improve relative quantitation and error bound estimates. For convenience we will here refer to the multiple peaks inherent in isotope and charge state variability as "multi-peak information." Multi-peak information could be used either by combining multiple peaks by summation of amounts from each peak before ratios or log-ratios are calculated. Multi-peak information could also be used by first calculating ratios or log-ratios for corresponding peaks (correspondence by isotope and/or by charge) and then using the resulting set of values to get the ratio or log-ratios using a measure of central tendency and to get the variability using statistical measures such as variance or interquartile range.

Calibration of the ratios might also be necessary, as ratios of AUC's and related measurements would not always be proportional to absolute quantity. In order to calibrate, we would have to estimate the function C that maps (AUC1, AUC2, ratio) to, for example, quantity1/quantity2. Here AUC1 and AUC2 are used to represent the measure total amount of signal for the conditions A and B, respectively, and could be calculated using AUC or any of the other methods above. The items quantitity1 and quantity2 represent the total amount of the same analyte present in the conditions A and B, respectively, and giving rise to the corresponding AUC1 and AUC2.

Calibration would be performed by starting with solutions of known, relatively pure analytes, such as digested peptides or mixtures of small molecules, in a variety of known quantities or concentrations and injection volumes spanning the region of interest. The values of AUC1 and AUC2 would be repeatedly measured using any of the above procedures using 1, using 2, using 3, using 4, using 5, or using more than 5 replicates for each sample. The resulting curves and error estimates would allow the mapping C to be estimated using standard techniques such as, for example, radial basis functions or regression. If desired, one or two variables in the domain of this mapping can be ignored.

Differences can be summarized in a variety of ways for use in classification or prediction. Examples would include AUC-like summarization described above including weighted sums of points that are "near" local maxima ("peaks"). Such data are often used to make numerical predictions such as for efficacy or toxicity or to classify such as predicting if a sample came from condition A or condition B for example disease vs. healthy or malignant vs. benign. One could choose features from the AUC-like or local maximum measures described above (this requires first finding significant differences), making such choice by estimating classifier performance using bootstrapping/jackknifing and/or cross-validation, and using a combinatorial or stochastic optimization to select the resulting features.

Combinatorial techniques would include incremental forward-feature selection (find the best one, then the best one to include with that, then the best to include with those two), n/m-way incremental forward selection (find the best subset of n, typically with n=1, n=2 or n=3, then the best m=1, 2, or 3 to include with them, continuing until the desired number of features or desired performance is found), or decremental backward selection which comprises starting with all features included, then iteratively removing the n features which degrade performance the least, where typically n=1, 2, or 3.

Stochastic optimization would include genetic algorithms or random forests for selection of features (after significant differences were found and summarized as, for example AUC's and/or local maxima and/or multi-peak features). The optimization could also be applied at the level of defining features so that, for example, a weighted sum of the signals in the curve is used to define the area under the curve, rather than an unweighted sum. The set of weights could be a function of the m/z and/or indices over which the summarization is being performed, but most simply would be a single weight kernel for modifying the AUC calculation based on, for example, distance from the local max in a significant difference or from the center of that difference (along the m/z- and/or index-axis).

Continuous optimization techniques like conjugate gradients and related methods could be used to optimize the discretizations of the weight functions by optimizing classifier or predictor performance as described above.

Stochastic methods such as simulated annealing or genetic algorithms could also be used to optimize these weight functions, as could singular value decomposition or logistic regression on these values for a fixed set of significant differences (and their neighborhoods in m/z and/or index values).

V. Data Presentation

Depending upon the performed methods and analysis, data can be presented in a variety of different formats. Examples of different formats include table and graphic formats.

In a preferred embodiment the results of LC-MS data analysis are displayed as a ranked list of differences with different columns specifying m/z, start and end elution times, and likelihood or log likelihood of each signal; more preferably the group, direction (A/B) and/or amount of change, and partition ("full shift," "half shift," "apparently valid result," or other representations of those three states) are also provided (see Example 2, Table 3, infra). In other embodiments additional information could be in the table, such as values or ranges of other indices, local or global time shift values, and/or other index alignment values. Additional optionally-displayed information could include measurements of overall data quality, versions of algorithms or software that were used, or values of baselines that were subtracted from signals before or during the process of calculating relative amounts, estimates of ranges of or errors in relative amounts or absolute amounts.

Figure 10:
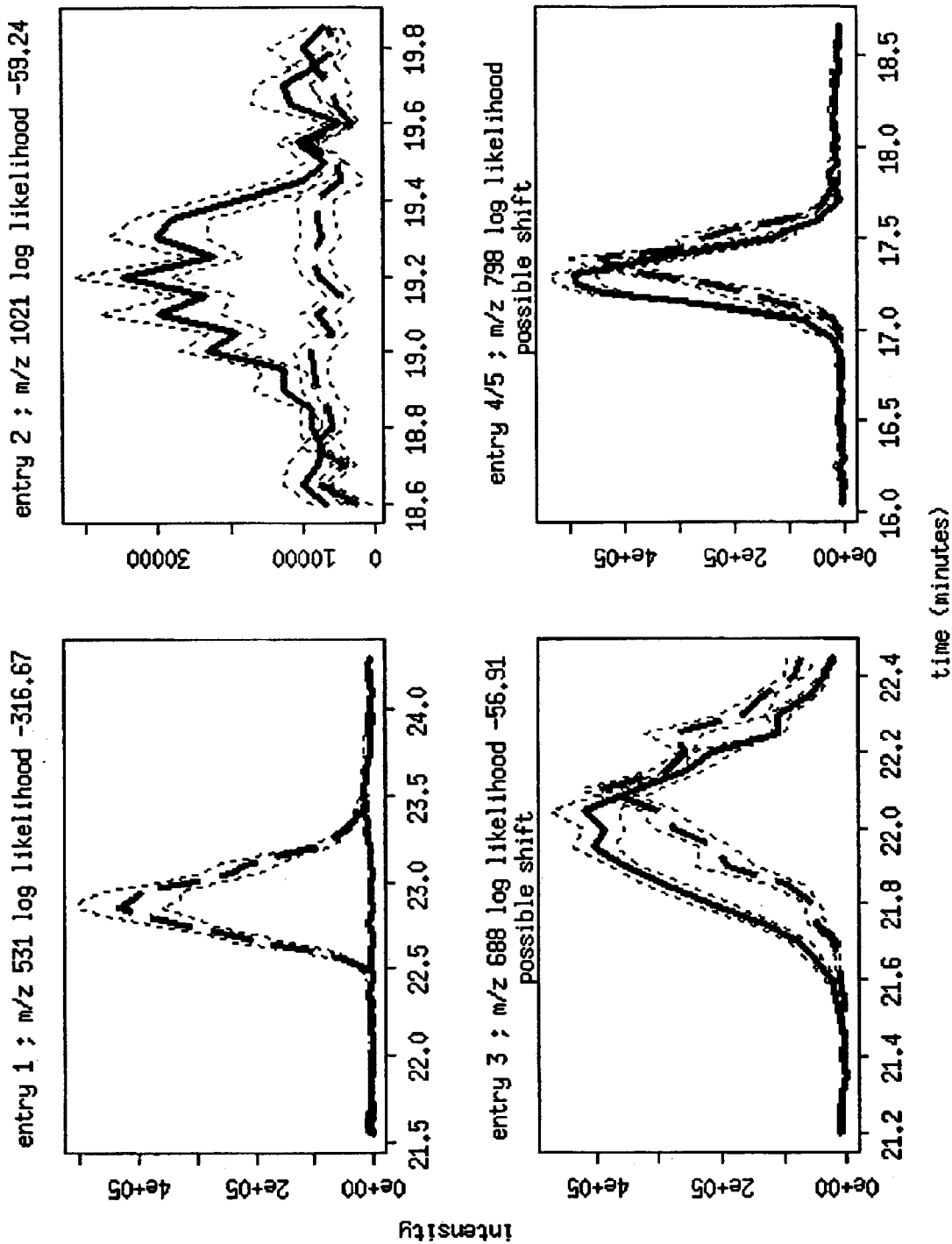
FIG. 10 illustrates different types of signal differences. Top panels: confirmed signals. Bottom left: half shift—shifted signal with half detected as significant. Bottom right: full shift—shifted signal with both halves detected.

Graphic presentations can also be employed. For example, for an m/z-intensity pair difference between spectra from two sample sets, the mean signals in the two sets of spectra and their standard deviations can be graphed, thereby creating a "signal plot". The graphs can be labeled as to their false-positive partition status, as shown in FIG. 10. In a preferred embodiment, these mean signals and deviations are plotted versus liquid chromatography elution time over a window including the region of significance plus that region's width on each side. Other summary statistics such as p-value could, in other embodiments, be plotted as functions of m/z identifiers, zero or more index variables, and/or experimental factors, and could be labeled and/or colored to indicate experimental factors and/or phenotype, genotype, and/or clinical data relating to samples or sample sets (see, for example, FIGS. 11, 12, 13, and 15).

Figure 11:
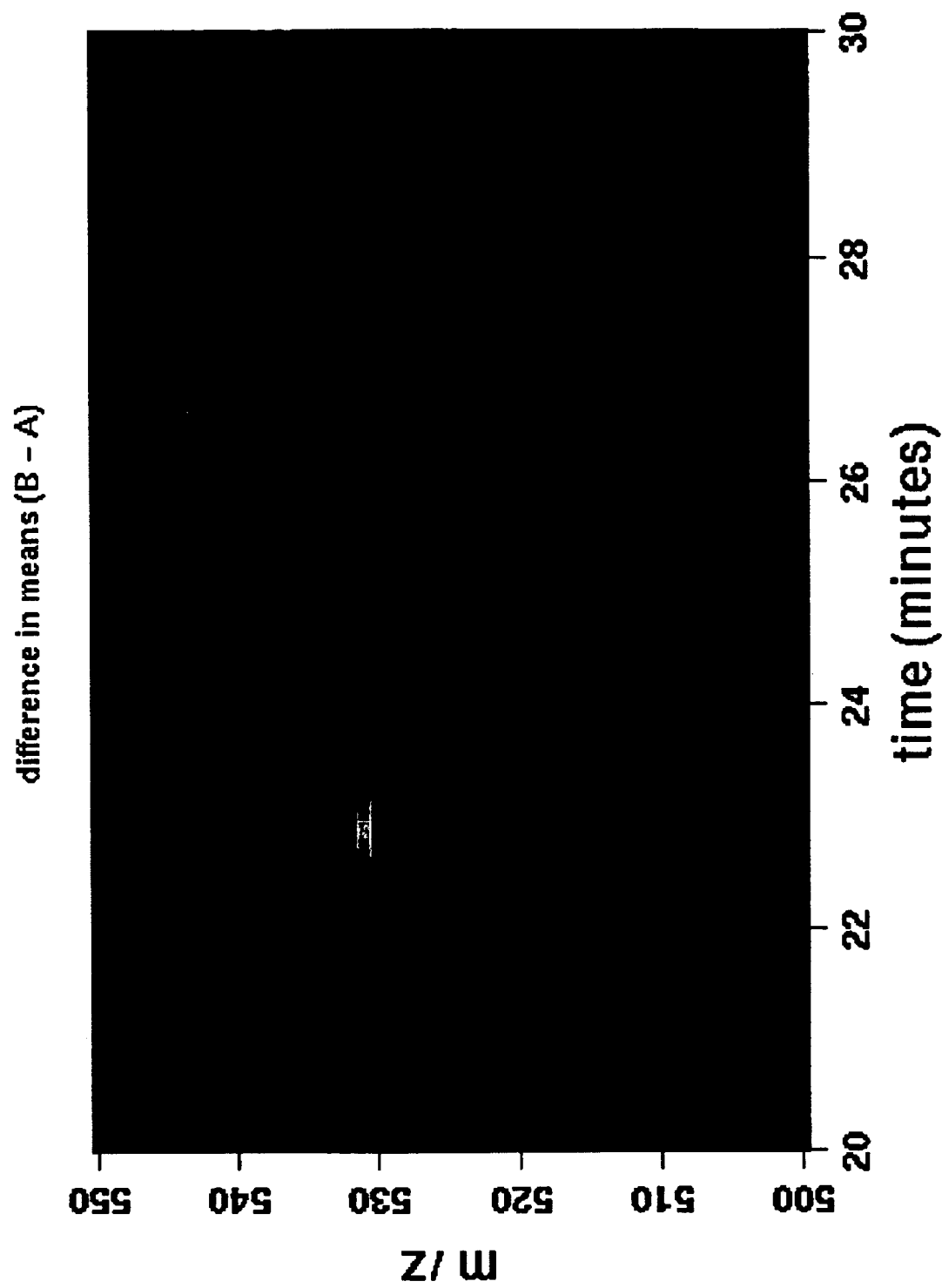
FIG. 11 illustrates differences in mean intensity values for a subset of time and m/z values.
Figure 12:
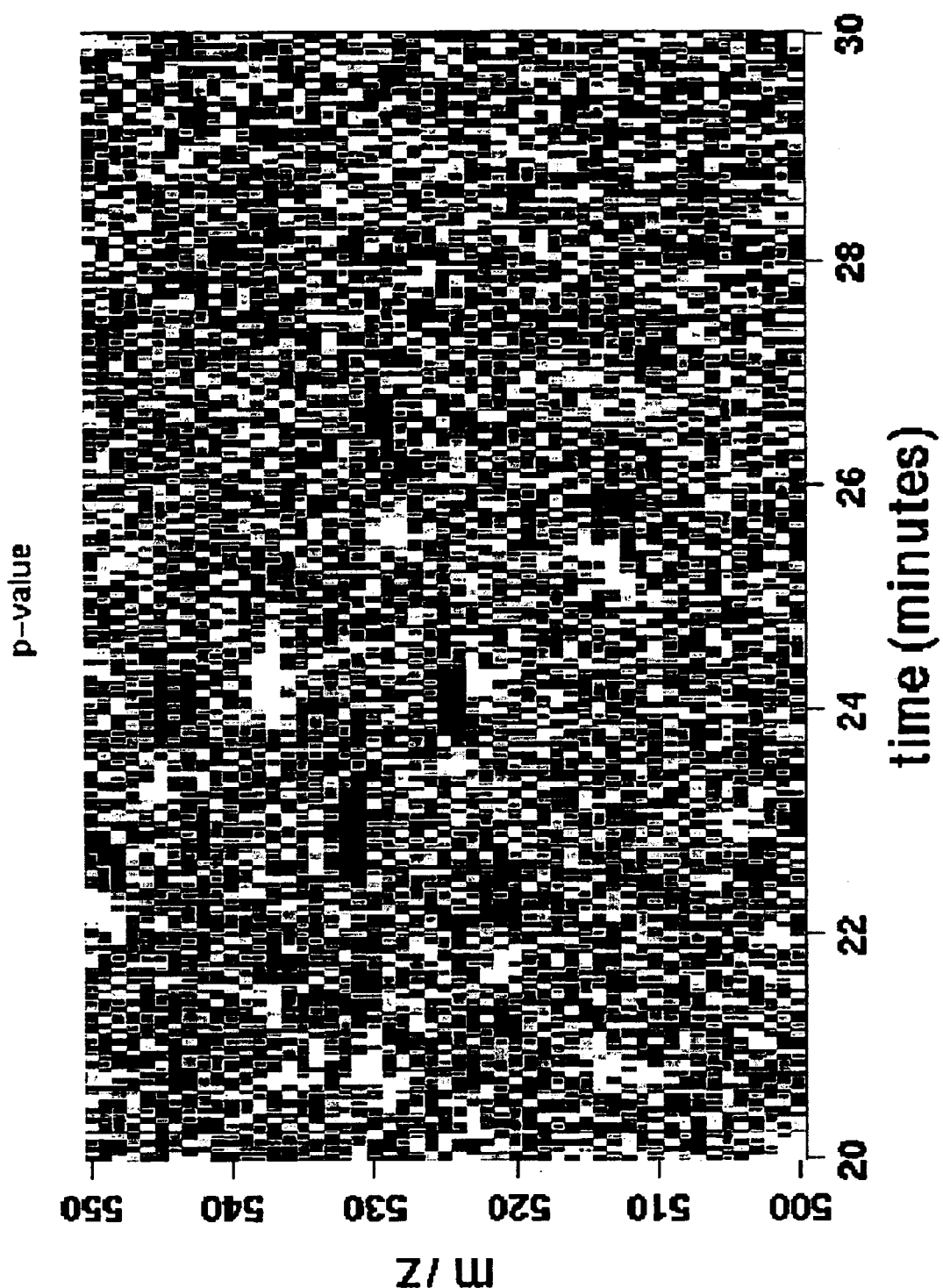
FIG. 12 illustrates p-value comparisons.
Figure 13:
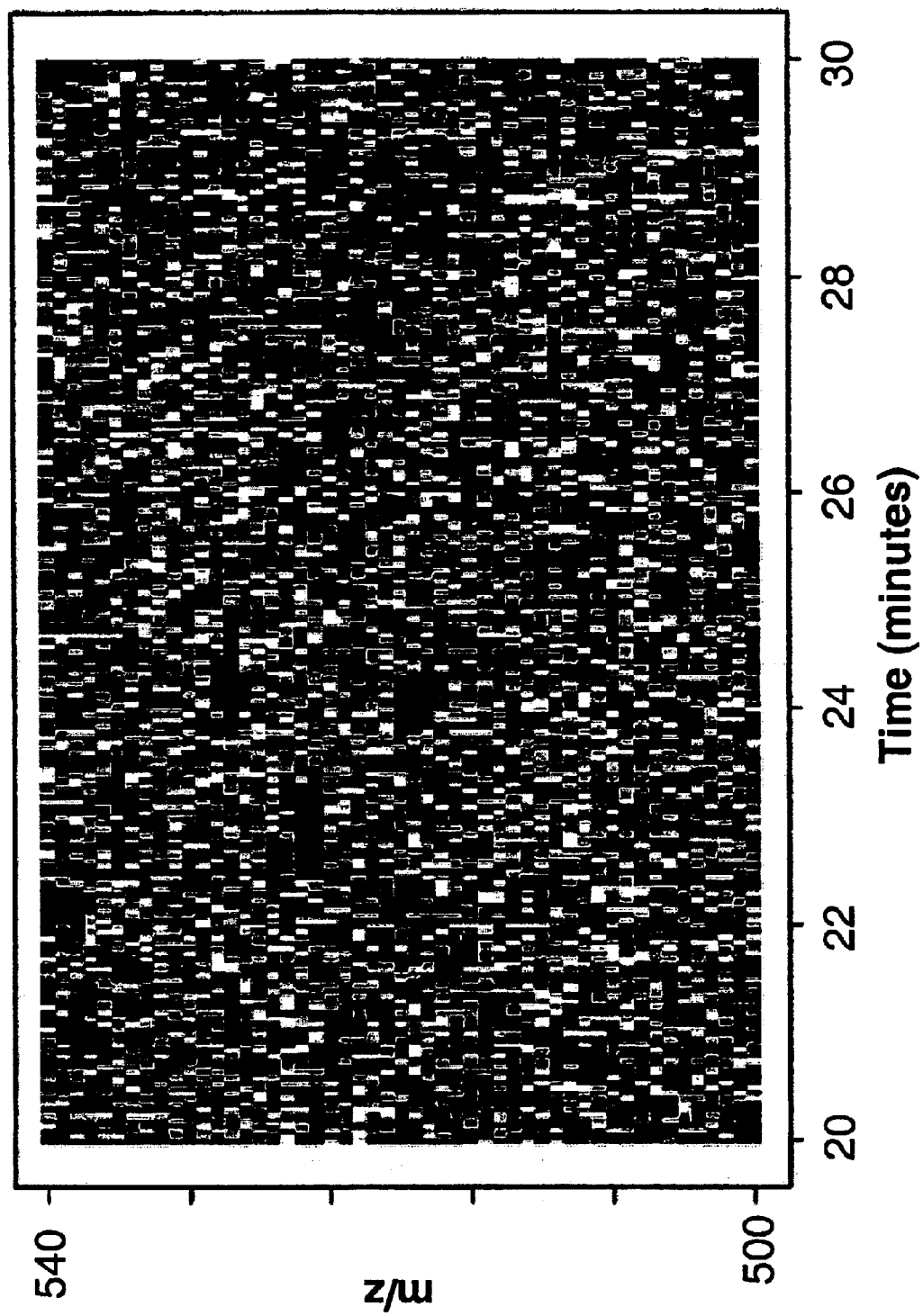
FIG. 13 illustrates magnitude and significance of differences together.

Another presentation method is intensity plots. Intensity plots are images in which hue, a symbol, intensity, and/or color are functions of the intensity, local time warping or related statistics (such as mean, median, p-value of difference, variance, or number of spectra with data in that region). FIGS. 11, 12, and 13 provide examples of intensity plots. Colors can be replaced or augmented, for example by black and white, grey scale, or symbols. If the desired information cannot be encoded by the intensity plot's available colors, hues, intensities, or symbols, multiple plots may be produced and placed near each other or overlaid using transparencies and/or electronic displays.

FIG. 11 illustrates differences in mean intensity values for a subset of time and m/z values.

FIG. 12 illustrates p-value comparisons. Time persistence can be visually noted by a "line" of particular intensity or color.

FIG. 13 illustrates magnitude and significance of differences.

The plots shown in FIGS. 11, 12, and 13 are for a subset of a data set. A larger subset, including the entire data set, could also be shown. Numerous variations are possible, such as:

(1) showing points (with color other than background) on the image only for regions around those specified in the ranked list;

(2) having the image consist only of "spots" centered at positions indicated by, or related to, those on the ranked list and with colors, borders, shapes, sizes, orientations, height above the t-m/z-plane, or other attributes varying with attributes of interest such as number of spectra with data in that region and statistical values; and (3) combinations of all above methods, possibly with geometric shapes or symbols superimposed on the image to indicate or label the location or other attributes of an identified difference.

The image and the ranked list could also be made dynamic so that when a user clicks on or otherwise indicates an item or group in the ranked list, the corresponding points on the graphs are visually emphasized to achieve one or more of the following:

(1) changing the color, hue, intensity, shape, or other attributes, or those of the background and/or other points on the image;

(2) one or more corresponding signal plots are shown; and (3) the total intensity chromatogram, mass chromatograms, total or partial signal chromatograms, p-values vs. t and/or m/z, or spectra or average spectra for one or more index variables, ranges of interest and m/z-intensity pairs of interest are shown.

The decision as to which graphs to display could be controlled by check boxes, radio buttons or other common interface elements, and can be done automatically, or they could be shown only when corresponding buttons or links are clicked. Further, the linking could allow the user to select, using a pointing device such as a mouse or tablet, a point or region on the image and then display any included significant differences and related graphs. Similarly one could select from the intensity or signal or mass chromatograms or spectra (total or local averages or other combinations) and be shown a table, an intensity plot, or a signal plot.

Any of the visualizations could make use of data which leaves multi-peak information separate, or data which combines information from the peaks first. For example, the signal plot in FIG. 10 could be based on the signals for an individual m/z identifier, or on a combination such as a summation of the signals for all identifiers relating to different isotopes of a given analyte as identified using any of the techniques above. Grouping information could also be indicated by giving group numbers to peaks such that these group numbers are unchanged among sets of peaks possibly representing the same analyte, or by drawing graphs (sets of edges and vertices, for example lattices) that indicate possible group relationships among peaks. Multiple group numbers or group number versions could be assigned to each peak where necessary to indicate that a peak might be grouped in more than one way. The interface could also provide evidence for the grouping such as correlations of peak shapes and allow the user to confirm or reject some grouping possibilities and store those user-annotations.

VI. Separation Techniques

Separation techniques separate analytes based on one or more analyte properties. Useful properties for separation techniques include one more of the following: size, charge, weight, hydrophobicity, polarity, and the presence or absence of particular chemical moieties. General separation technique formats include centrifugation, fractionation, chromatography, gel electrophoresis, hydrophobic interaction chip, gas phase ion mobility, gas phase ion reactions, and affinity chips.

In an embodiment of the present invention, spectra are acquired using chips such as a hydrophobic interaction chip or an affinity chip to capture analytes based on general properties or particular moieties. Spectra can be taken on the chip by, for example, surface enhanced laser desorption/ionization. (Petricoin et al., *The Lancet* 359:572–577, 2002.)

In another embodiment of the present invention, chromatographic separation is employed. Chromatography involves the separation of a liquid or gaseous chemical mixture into components as a result of differential distribution of the solutes as they flow around or over a stationary liquid or solid phase or through a partial or complete vacuum.

A preferred chromatographic technique is liquid chromatography, which can be coupled to mass spectrometry. Liquid chromatography in addition to separating analytes also can provide an index (e.g., time) that can be used to facilitate selectively identifying analytes having a different level of abundance between sample sets.

Various mass spectrometric techniques can be applied in conjunction with different liquid chromatographic techniques. Examples of mass spectrometric techniques that can be interfaced with liquid chromatography include electrospray ionization, nanospray ionization, atmospheric pressure chemical ionization, and photoionization. (Lim et al., *Biol. Pharm Bull* 25)(5):547–557,2002.)

Examples of different liquid chromatographic techniques include reverse phase high performance liquid chromatography, capillary electrophoresis, capillary electrochromatography, cation-exchange chromatography, anion-exchange chromatography, size-exclusion chromatography, and affinity based chromatography. (Lim et al., *Biol. Pharm Bull* 25(5):547–557, 2002; Link, *Trends in Biotechnology* 20(12, *Suppl*):S8–S13, 2002.)

Analyte separation can be enhanced using multidimensional liquid chromatography. Multidimensional liquid chromatography typically relies on using two or more independent physical properties of an analyte. (Link, *Trends in Biotechnology* 20(12, *Suppl*):S8–S13, 2002.) Multidimensional liquid chromatography can be performed, for example, by carrying out two or more different liquid chromatography steps in a single separation device by changing two or more solvent properties in a specified sequence (Link et al., *Nature Biotechnology* 17:676–682, 1999).

VII. Additional Techniques

If desired, additional techniques can be performed to further characterize analytes of interest. Further characterization can be performed, for example, to determine the identity or chemical structure of a particular analyte whose expression level changes between sample sets.

Analytes, such as polypeptides, can be further characterized using techniques such as tandem mass spectrometry. Tandem mass spectrometry involves the use of multiple stages of mass spectrometry to further analyze a particular ion or ions at a particular m/z. It is common practice to record an initial mass spectrum to permit the identification of a parent ion(s) of interest. Further analysis involves converting the parent ion into products and analyzing the resulting product ions by mass spectrometry.

Results generated from mass spectrometry can be used for analyte identification. For example, the results can be compared to a database containing predicted mass spectra for smaller components. Techniques for performing tandem mass spectrometry, including the optional use of isotope tagging are well known in the art. (Yates et al., U.S. Pat. No. 5,538,897, Smith *Trends in Biotechnology* 20(12, *Suppl*):S3–S7, 2002, Flory et al., *Trends in Biotechnology* 20(12, *Suppl*):S8–S13, 2002.) A database of identified analytes and their index and m/z values can be created and employed, so that future analytes can be putatively identified by searching against the database for previously identified analytes with similar patterns of index values or m/z values.

VIII. Applications

Selectively identifying analytes having different abundances between two samples has a variety of different uses in different fields. Two general field classifications, which to some extent overlap, are (1) biological and (2) qualitative.

Examples of biological applications include:

1) Comparison of proteomes with modulated states;
2) Evaluating drug metabolism and metabolite changes;
3) Measuring post- or co-translational modifications;
4) Comparing healthy and disease states, different disease states, or different healthy states;

5) Measuring altered protein abundance;

6) Measuring protein primary sequence modification;

7) Measuring changes in biological activity;

8) Measuring the effects of genetic manipulation;

9) Performing dosage or time course studies of treatment of cells or animals;

10) Identifying the presence of biological warfare agents;

11) Identifying compounds which have a particular affinity for a given biological material, especially identifying the level or existence of such affinities for a large number of compounds;

12) Identifying compounds which have an effect on a biological system, especially identifying the level or existence of such effects for a large number of compounds; and 13) Identifying biological materials which are changed (e.g. metabolized, lysed, or otherwise modified) by a given biological system or substance or chemical substance, especially identifying the level or existence of such changes for a large number of materials, especially with respect to the use of protein or peptide or other chemical or biological libraries to identify enzyme substrates.

Examples of qualitative uses include:

1) Detecting known or unknown contaminants in water, air, soil, or clothing;

2) Identifying the presence of chemical warfare agents;

3) Identifying differences or impurities in raw materials or manufactured products; and 4) Identifying components in air in buildings or other enclosed spaces.

Analytes can be modified or unmodified prior to analysis. Analyte modification can be performed to add a tag facilitating analyte analysis, detection or purification. Tagging could be used, for example, to increase sensitivity or specificity or to otherwise change the attributes required to differentiate analytes between sample sets. Examples of tags include fluorescent, radioactive, associative, affinity, covalent, and isotopic tags. Tags can be used to, for example, mark samples under one condition or differentially mark samples for a number of conditions.

Particular areas of biological and qualitative applications include: (A) diagnostic applications; (B) compound evaluation and pharmacology including reverse pharmacology; and (C) disease treatment.

A. Diagnostics

The analytical techniques described herein can be used in performing diagnostic analysis and in identifying markers for diagnostic analysis. Diagnostic analysis can be performed by measuring the presence or amount of a marker associated with a disease or disorder. A marker can be based on a single or multiple analytes. Biological analytes present inside, in or on the surface of, or outside a cell, such as nucleic acids or peptides, are potential markers.

A marker associated with a disease or disorder means having predictive power for: (1) the presence or level of a disease or disorder; or (2) a greater potential than the general population, or an identifiable subpopulation, for contracting a disease or disorder. Different types of markers can be measured to determine whether an association exists including markers attributed to a causative agent, markers directly involved in disease and disorder, and/or markers reflecting a disease or disorder state.

Causative agents include host agents and agents introduced into a host. Host agents associated with a disease or disorder include toxic agents that are produced in a host; and agents over or under produced relative to a healthy individual.

Outside agents that can cause a disease or disorder include chemical substances, prions, bacteria, fungi, archea, and viruses, as well as electromagnetochemomechanical fields, ionizing radiation or other teratogenic or toxic or incapacitating entities. The different organisms or resulting damaged genetic material contain or encode peptides. Measuring the presence or production of such peptides (as well as, potentially, other chemical entities) can be used to indicate the presence of a disease or disorder or the potential for contracting a disease or disorder due to the causative agent.

Host responses to outside agents are another source of biological markers. Host responses may include the production of immune-response agents including immunoglobulins or a change in the host level peptides.

Biomarkers associated with a disease or disorder can be selected based on prior knowledge of a causative agent or can be empirically determined. The possible association between one or more markers and a disease or disorder can be assessed with statistical, other computational, or graphical methods.

Different types of sample sets can be employed to identify biomarkers associated with a disease or order. Possible subject groups include subjects previously identified at an increased risk of a disease or disorder and subjects having a particular disease or disorder. Sample sets can also be defined using risk levels for contracting a disease or disorder and clinical levels of a disease or disorder. Subject groups can also be chosen at random from available populations with sample biases inherent in any approvable sampling procedure. (See also Section I. B. "Sample Sets" supra.)

The ability to analyze large amounts of data using the techniques described herein facilitates identification of potential biomarkers because it identifies analytes likely to have different levels in different types of samples. The association of potential biomarkers with a disease or disorder can be further evaluated using analysis techniques such as hierarchical and non-hierarchical clustering, agglomerative and divisive clustering, hybrids of the aforementioned clustering methods, measures of correlation or association, principal components or principle least squares analysis, Bayesian classifiers, classification and regression trees, random forests, linear or quadratic discriminant analysis, neural networks, patient rule induction methods, Bayesian networks, and belief networks. (See for example, T. Hastie, R. Tibshirani & J. Friedman. The Elements of Statistical Learning. Springer Series in Statistics. Springer, New York, 2001; B. D. Ripley, Pattern Recognition and Neural Networks, Cambridge University Press; 1996; Judea Perl Bayesian Networks, 1988; Bayesian Networks and Decision Graphs by F. Jensen, Springer Verlag, 2001.)

B. Compound Evaluation and Pharmacology

Compound evaluation and pharmacology can be performed to evaluate compound metabolism and effects on a cell or animal. Metabolic studies include the determination by sampling of biological materials the absorption, distribution, metabolism, and excretion of a compound and its metabolic by-products. Such evaluations have a variety of different uses including identifying important therapeutic targets, prioritizing potentially therapeutic compounds, identifying toxic metabolites, identifying therapeutic metabolites, identifying increased or decreased production of analytes that may harm a cell or animal and identifying increased or decreased production of analytes providing a beneficial effect to a cell or organism.

Compound reverse pharmacology can be performed using compounds with known effects to determine new therapeutic targets or new uses for one or more known compounds. Such studies could involve the identification of biomarkers for an unintended effect, beneficial or not, of a therapeutic intervention.

C. Disease Treatment

The expression state of biomarkers, such as peptides, provides information on the health of a cell or animal. Changes in the biomarker levels can be used to select particular treatments and to monitor treatment efficacy. The changes can be, for example, with respect to an untreated subject, different subjects at different states of treatment, or a subject at different times during treatment.

IX. Software

Computer implementation of different embodiments of the analysis described herein can be achieved using a computer program providing instructions in a computer readable form. An example of a high level view of the implementation of different variations is shown in the flow charts provided in FIGS. 1–9.

Different types of computer language can be used to provide instructions in a computer readable form. For example, the computer program can be written using languages such as S, C, C++, FORTRAN, PERL, HTML, JAVA, UNIX or LINUX shell command languages such as C shell script, and different dialects of such languages. "R," an S language dialect, is an example of a dialect with attributes facilitating analyses like those presented here (see http://cran.us.r-project.org).

Different types of computers can be used to run a program for performing analysis techniques described herein. Computer programs for performing analysis techniques described herein can be run on a computer having sufficient memory and processing capability. An example of a suitable computer is one having an Intel Pentium®-based processor of 200 MHZ or greater, with 64 MB or more main memory. Equivalent and superior computer systems are well known in the art.

Standard operating systems can be employed for different types of computers. Examples of operating systems for an Intel Pentium®-based processor includes the Microsoft Windows™ family such as Windows NT, Windows XP, and Windows 2000 and LINUX. Examples of operating systems for a Macintosh computer includes OSX, UNIX and LINUX operating systems. Other computers and their operating systems are well known in the art. In different embodiments, the R language is used on an Intel-based computer with 4 GB ram dual 866 MHz Pentium III processors running the LINUX-operating system or an IBM computer running the AIX operating system with an Intel-based computer running the Windows NT or XP operating system as an x-windows terminal.

X. EXAMPLES

Examples are provided below to further illustrate different features of the present invention. The examples also illustrate useful methodology for practicing the invention. These examples do not limit the claimed invention.

Example 1

Analysis Techniques

There are many statistical methods for determining if two sets of numbers are significantly different. (Kanji, 100 Statistical Tests, 1999, SAGE Publications, W. J. Conover. Practical nonparametric statistics (2nd ed.). New York: John Wiley & Sons, 1980.) This example illustrates using within-sample-set variability and between-sample-set variability to determine the statistical significance of differences. The example illustrates a t-test and then a Wilcoxon rank sum test.

All of the calculations in this section are demonstrated on the example data in Table 1. The numbers for the calculation were selected for illustration purposes.

The columns labeled I(A, 1), I(A, 2), ... I(A, 5) represent 5 measurements of intensity (binned and normalized) for sample set A, and similarly for I(B,1) through I(B,5) and sample set B. The means of these numbers are in the columns mean(A) and mean(B). Mean (A) was calculated as follows:

$$\mathrm{mean}(A) = \frac{1}{n_A} \sum_{j=1}^{n_A} I(A, j), n_A = 5$$

Mean (B) was calculated in an analogous manner.

The difference between the two sets of measurements can be represented in part by the differences in the means: D=mean(A)−Mean(B). To decide whether or not this difference D is significantly different from zero, one statistical approach is to determine how likely it is to find a difference of this size by chance.

Given the measurements and some statistical assumptions, the probability of finding a difference at least as large as D due to random chance (e.g. noise) can be calculated as shown below. This probability is called a "p-value," and a difference is typically considered significant if the p-value is less than 0.05, though other thresholds can be used depending on the application.

In general, if D is small compared to the "spread" or "variability" of A and B, then finding a difference at least as large as D is considered too likely to be a random coincidence, and therefore insignificant (FIGS. 14A, 14B). If D is sufficiently large compared to the "spread" or "variability" of A and B, then it is unlikely to have happened by chance, and is deemed significant (FIGS. 14C, 14D).

Thus, the within-sample-set variability (spread of the A measurements and the spread of the B measurements) is being compared to the between-sample-set variability represented by D (and the spread of all 10 points considered together).

For the t-test, the measure of the within-set variability for sample set A is Dev(A) is the sample deviation:

$$\sigma_A = \mathrm{Dev}(A) = \sqrt{\frac{1}{n_A - 1} \sum_{j=1}^{n_A} (I(A, j) - \mathrm{Mean}(A))^2}$$

from which we calculate $$S_A = \sigma_A / \sqrt{n_A}$$

with $n_A=5$ in the current example. The symbols used in this section correspond to Table 1 and to those in the flowcharts in FIGS. 1–9.

$S_A$ is a measure of how widely spread the measurements are about the mean. If all of the measurements are identical, this number is zero. If not, it gives an estimate of the width of a best-fit bell-shaped curve ("Gaussian" or "Normal") representing the distribution (spread pattern) of data in sample set A. A similar calculation is done for B.

To determine how big D is relative to $S_A$ and $S_B$, we combine these into $$\sigma_D = \sqrt{S_A^2 + S_B^2}$$

and then find $$\tilde{D} = D/\sigma_D$$

The statistical significance of $\tilde{D}$ can be found by calculating its probability (the p-value) in a t-distribution. This requires also knowing the number of "degrees of freedom," F, which takes into account the number of measurements and differences between $S_A$ and $S_B$.

$$F = \frac{\sigma_D^4}{\frac{S_A^4}{n_A - 1} + \frac{S_B^4}{n_B - 1}}$$

In practice the p-value can be calculated based on $\tilde{D}$ and F using functions in standard spreadsheet applications, or looking up values in a table.

The values have been calculated for 8 examples labeled p1, p2, . . . , p8 in Table 1. In a typical LC-MS application with a time index variable, t, p1 and p2 would be dropped from consideration even though they are below a typical p-value threshold of 0.05. This is because these significances (of differences) do not persist over time (assuming that Table 1 is complete). Points p3 through p7 share a single m/z identifier and have a run of 5 consecutive times and with a statistical significance less than a typical threshold of 0.05, so that these 5 points together could cause the m/z 502.1 to be flagged as having a significant difference with start time 3 and end time 3.2.

6 (instead of 5) consecutive times with significant differences were required as a criterion to flag an m/z and start and end time as significant, then this would be missed. However, in point p8 all 5 A values are below 2000, while all 5 B values are above 2000. The reason that the t-test failed to find this significant is that an underlying assumption about the distributions of points ("normality") is violated. This test is said to not be "robust" since one or two "outliers" (rare, different measurements) can cause it to give undesirable results.

An example of an alternative test which makes less stringent assumptions about the data is the Wilcoxon rank sum test. (Kanji, 100 Statistical Tests, 1999, SAGE Publications; W. J. Conover, Pratical nonparametric statistics (2nd ed.). New York: John Wiley & Sons, 1980). To apply this test, rank the 10 measurements 1 through 10 from smallest to largest (Table 2):

TABLE 2

| Rank | Sample | Measurement |
|---|---|---|
| 1 | A | 1959.80 |
| 2 | A | 1994.12 |
| 3 | A | 1997.14 |
| 4 | A | 1997.53 |
| 5 | A | 1999.09 |
| 6 | B | 2000.64 |
| 7 | B | 2000.69 |
| 8 | B | 2001.11 |
| 9 | B | 2001.77 |
| 10 | B | 2098.51 |

Then add up the ranks of the A's to get 1+2+3+4+5=15. This sum gives us a measure of the between sample variability relative to the within sample variability because it considers how the measurement compare to each other. The value 15 can be looked up in a table for this test to find out that this sequence is significant with a p-value less than 0.01. In practice one could take the smaller p-value from a set of

TABLE 1

| | | Point name | | | | | | | |
|---|---|---|---|---|---|---|---|---|---|
| | | p1 | p2 | p3 | p4 | p5 | p6 | p7 | p8 |
| | m/z | 300 | 423.776 | 502.1 | 502.1 | 502.1 | 502.1 | 502.1 | 502.1 |
| | Time | 4.75 | 3 | 3 | 3.05 | 3.1 | 3.15 | 3.2 | 3.25 |
| Sample Set A | I (A, 1) | 500.27 | 1963.48 | 1996.52 | 4976.35 | 10037.68 | 5007.39 | 2011.89 | 1986.77 |
| | I (A, 2) | 500.74 | 1989.75 | 2020.20 | 4990.82 | 10095.35 | 5037.05 | 1969.72 | 1989.10 |
| | I (A, 3) | 499.83 | 1990.27 | 2001.13 | 4987.53 | 10017.86 | 5013.46 | 2016.94 | 1987.94 |
| | I (A, 4) | 501.68 | 1984.70 | 1996.01 | 5038.81 | 9957.34 | 4986.91 | 2024.44 | 1996.56 |
| | I (A, 5) | 501.39 | 1966.31 | 1995.37 | 4988.38 | 10109.80 | 4999.65 | 1995.48 | 1997.15 |
| within sample variation | Mean (A) | 500.78 | 1978.90 | 2001.84 | 4996.38 | 10043.61 | 5008.89 | 2003.69 | 1991.50 |
| | Dev (A) | 0.77 | 13.01 | 10.51 | 24.37 | 61.64 | 18.60 | 21.76 | 4.96 |
| | S_A | 0.34 | 5.82 | 4.70 | 10.90 | 27.57 | 8.32 | 9.73 | 2.22 |
| Sample Set B | I (B, 1) | 499.31 | 100037.61 | 2030.99 | 99608.88 | 100337.00 | 99283.86 | 2011.50 | 2001.47 |
| | I (B, 2) | 501.11 | 98331.30 | 2008.54 | 99930.69 | 99983.94 | 99527.27 | 2023.62 | 2005.52 |
| | I (B, 3) | 498.20 | 100189.46 | 2032.56 | 99623.42 | 100832.95 | 99433.99 | 2039.06 | 2001.50 |
| | I (B, 4) | 499.29 | 100299.32 | 2016.89 | 99742.87 | 98536.52 | 97831.09 | 2041.42 | 2002.21 |
| | I (B, 5) | 497.99 | 98985.87 | 2016.63 | 99376.77 | 98468.98 | 101809.46 | 2064.17 | 2075.27 |
| within sample variation | Mean (B) | 499.18 | 99568.71 | 2021.12 | 99656.52 | 99631.88 | 99577.14 | 2035.95 | 2017.20 |
| | Dev (B) | 1.24 | 867.45 | 10.30 | 202.64 | 1074.23 | 1426.62 | 19.91 | 32.51 |
| | S_B | 0.55 | 387.94 | 4.61 | 90.62 | 480.41 | 638.00 | 8.90 | 14.54 |
| Between-Sample Variation | Sigma_D | 0.65 | 387.98 | 6.58 | 91.27 | 481.20 | 638.06 | 13.19 | 14.71 |
| | D = Mean (B) − Mean (A) | −1.60 | 97589.81 | 19.28 | 94660.14 | 89588.27 | 94568.24 | 32.26 | 25.69 |
| | D/Sigma_D | −2.47 | 251.53 | 2.93 | 1037.09 | 186.18 | 148.21 | 2.45 | 1.75 |
| Significance | F | 6.68 | 4.00 | 8.00 | 4.12 | 4.03 | 4.00 | 7.94 | 4.19 |
| | p-value | 0.0447 | 0.0000 | 0.0190 | 2.64E−12 | 4.48E−09 | 1.24E−08 | 0.0405 | 0.1523 |

Point p8 has a p-value of approximately 0.15, significantly above any commonly used threshold. Thus if a run of p-values calculated from different tests. This would increase sensitivity (more points would be detected), but suitable corrections in the estimated log-likelihood (such as Bonferroni) could be required.

Example 2

Analysis of a Prepared Protein Mixture

This example employs synthetic isolated or purified protein sample sets to illustrate selective identification of analytes having a different level of abundance between sample sets in the presence of complex mixtures of analytes. The example utilizes a time index in addition to m/z-intensity pairs, and illustrates the results of different filtering techniques that can be used to reduce false positives while maintaining a high degree of sensitivity to small signals in the spectra corresponding to relatively low levels of analyte differences.

Protein Digest Standards

Tryptic digests of twenty four proteins were obtained from Michrom BioResources (Auburn, Calif.). The proteins, sources, and corresponding molecular weights selected were Cytochrome C (Equine) 12 kDa, Lysozyme (Chicken) 14 kDa, Hemoglobin (Bovine) 17 kDa, Myoglobin (Equine) 17 kDa, Beta-Lactoglobulin (Bovine) 18 kDa, Chymotrypsinogen (Bovine) 25 kDa, Carbonic Anhydrase (Bovine) 29 kDa, Deoxyriboneuclease (Bovine) 31 kDa, Carboxypeptidase A (Bovine) 35 kDa, Glyceraldehyde 3P Dehydrogenase (Rabbit) 37 kDa, Conalbumin (Chicken) 40 kDa, Peroxidase (Horseradish) 44 kDa, Alpha Amylase (Bacillus) 50 kDa, Glutathone S-Transferase (Equine) 51 kDa, Glutamic Dehydrogenase (Bovine) 55 kDa, Bovine Serum Albumin (Bovine) 68 kDa, Apotransferrin (Bovine) 76 kDa, Lactoperoxidase (Bovine) 85 kDa, Amyloglucosidase Aspergillus 92 kDa, Phosphorylase B (Rabbit) 97 kDa, Beta Galactosidase (Bovine) 115 kDa, Catalase (Bovine) 128 kDa, Lactic Dehydrogenase (Rabbit) 140 kDa, Immuno-gamma-globulin (Porcine) 160 kDa. Each sample was stored frozen at −80° C.

Peptide Standards

Lyophilized bradykinin 1–9 (MW=1060 u), Angiotensin I (MW=1296), and neurotensin (MW=1672) were obtained from Sigma-Aldrich (St. Louis, Mo.). The peptides were combined and reconstituted with 0.1% triflouroactetic acid (TFA) to produce a 10 pm/uL stock solution.

Combination of Protein Digests

A 50 pm/uL solution was prepared by adding a 10 uL aliquot of 0.1% TFA to approximately 500 pmol of each of the following twenty protein digest standards: Cytochrome C, Lysozyme, Hemoglobin, Beta-Lactoglobulin, Chymotrypsinogen, Carbonic Anhydrase, Deoxyriboneuclease, Carboxypeptidase A, Glyceraldehyde 3P Dehydrogenase, Peroxidase, Glutathone S-Transferase, Glutamic Dehydrogenase, Apotransferrin, Lactoperoxidase, Amyloglucosidase Aspergillus, Phosphorylase B, Beta Galactosidase, Catalase, Lactic Dehydrogenase, Immuno-gamma-globulin. The protein digest stock solutions were combined to obtain a 2.5 pmol/uL mixture of the 20 protein digests. This mixture was split into two identical 100 uL aliquots that were denoted protein mixture A and B.

Additions to Protein Mixture A (Sample Set 1)

Stock solutions of myoglobin (50 pm/uL), conalbumin (10 pm/uL), alpha amylase (5 pm/uL), and bovine serum albumin (1 pm/uL) were prepared by the reconstitution of approximately 500 pm of each lyophilized protein digest with 10, 50, 100, and 500 uL of 0.1% TFA, respectively. A 10 uL aliquot of each stock solution was added to 100 uL of protein mixture A. The final volume of stock solution A was brought to 150 uL with the addition of 10 uL of 0.1% TFA. The final calculated concentration of the digested proteins in protein mixture A are as follows: [20 protein mix]=1.7 pm/uL, [myoglobin]=3 pm/uL, [conalbumin]=0.7 pm/uL, [alpha amylase]=0.3 pm/uL, [bovine serum albumin]=0.07 pm/uL.

Additions to Protein Mixture B (Sample Set 2)

A 35 uL aliquot of a 10 pm/uL solution of conalbumin was added to 100 uL of protein mixture B. In addition, a 10 uL aliquot of the 10 pm/uL peptide stock was added to protein mixture A and the final volume was increased to 150 uL with a 5 uL addition of 0.1% TFA.

Liquid Chromatography Mass Spectrometry Protocol

Samples were analyzed using an analytical liquid chromatograph (HP1100, Agilent Technologies, Palo Alto, Calif.) and quadrupole ion trap mass spectrometer (LCQ; ThermoFinnigan, San Jose, Calif.). Samples were injected onto a C18 reverse phase column (Brownlee OD-300, Aquapore, C18, 7 mm, 300a, 5 cm×1.0 mm; Perkin Elmer, Wellesley, Mass.) and separated with a binary gradient of 0.1% TFA (solvent A) and acetonitrile (solvent B) at a flow rate of 100 uL/min. The gradient increased from 0 to 70% solvent B in 45 minutes and the elluant was directed into the electrospray ionization source of the mass spectrometer. Full scan centroided mass spectra were acquired every 1.2 seconds over an m/z range of 400 to 1800 Da/z. The LC-MS data files were converted from an instrument specific format to a text file that contains retention time, m/z, and intensity data in three columns, as well as other ancillary information used to identify the experiment and/or sample.

Replicate Mixture Analysis

The HPLC autosampler was used to collect replicate spectra of the peptide standard, and protein samples A and B. The following injection order was used: blank sample, peptide standard, peptide standard, protein mix A, protein mix B, protein mix A, protein mix B, protein mix A, protein mix B, protein mix A, protein mix B, protein mix A, protein mix B, protein mix A, protein mix B, protein mix A, protein mix B, protein mix A, protein mix B, protein mix A, protein mix B, protein mix A, protein mix B, and peptide standard. The blank sample at the start helps to increase the consistency of retention times, while the peptide standards help to verify that consistency. Other orders could have been used.

Characterization of Individual Protein Digests

A 1 pm/uL solution of myoglobin, conalbumin, alpha amylase, and bovine serum albumin was prepared by addition of a 500 uL aliquot of 0.1% TFA to 500 pmol of each lyophilized protein digests. Each individual protein digest was analyzed using the LCMS protocol.

Results

Two hundred and four differences were detected between the mass-spectrometric signals from the two protein mixtures. A single re-alignment step was performed, resulting in 113 differences. Most of the eliminated differences were full or half shifts. Each intentionally introduced chemical difference between the two protein mixtures gave rise to multiple differences in the mass-spectrometric signals. Conversely, almost every difference between the mass-spectrometric signals was positively identified as arising from one of the known differences between the two protein mixtures.

Results of the analysis performed using the even numbered steps of the methods illustrated in FIGS. 1A and 2–6 are exemplified in table form and graphically. Table 3 shows some of the results in a tabular form. FIG. 10 illustrates four of the results in a figure form.

Table 3 provides for "group", "mass", "start", "end", "log likelihood", "Higher in A/B" and "Shift". Different variations of Table 3 are possible including those providing more or less information. A shift of zero indicates results automatically determined to be most likely due to difference in chemical composition of the two sample sets. A shift of "0.5" indicates half shifts (see "Partitioning," Section II.G supra), and could in general show the partition with respect to confidence or likelihood of false positive. A "1" would indicate a full shift, but after re-alignment this data set did not have any full shifts.

TABLE 3

| Group | Mass | Start | End | Log likelihood | Higher in A/B | Shift |
|---|---|---|---|---|---|---|
| 1 | 531 | 22.4 | 23.35 | −326.52 | B | 0 |
| 1 | 532 | 22.5 | 23.15 | −133.41 | B | 0 |
| 1 | 1061 | 22.65 | 22.9 | −41.76 | B | 0 |
| 2 | 649 | 28.3 | 29.35 | −323.94 | B | 0 |
| 2 | 650 | 28.35 | 29.25 | −233.17 | B | 0 |
| 2 | 433 | 28.45 | 29.2 | −164.53 | B | 0 |
| 2 | 434 | 28.55 | 29.15 | −115.67 | B | 0 |
| 2 | 651 | 28.9 | 29.15 | −29.65 | B | 0 |
| 3 | 804 | 23.85 | 24.75 | −273.71 | A | 0 |
| 3 | 805 | 23.8 | 24.5 | −197.99 | A | 0 |
| 3 | 537 | 23.95 | 24.6 | −149.65 | A | 0 |
| 3 | 806 | 24.1 | 24.35 | −42.39 | A | 0 |
| 3 | 805 | 24.6 | 24.85 | −37.67 | A | 0 |
| 4 | 637 | 20.65 | 21.5 | −257.65 | A | 0 |
| 4 | 638 | 20.75 | 21.35 | −116.41 | A | 0 |
| 4 | 636 | 20.95 | 21.25 | −53.26 | A | 0 |
| 5 | 690 | 32.85 | 33.6 | −236.26 | A | 0 |
| 5 | 691 | 32.65 | 33.6 | −226.72 | A | 0 |
| 6 | 837 | 27.25 | 28.2 | −220.99 | B | 0 |
| 6 | 838 | 27.3 | 28.15 | −209.27 | B | 0 |
| 6 | 559 | 27.3 | 28.15 | −164.45 | B | 0 |
| ... | ... | ... | ... | ... | ... | ... |
| ... | ... | ... | ... | ... | ... | ... |
| 81 | 720 | 22.15 | 22.4 | −33.06 | B | 0 |
| 84 | 1226 | 32.75 | 33 | −28.41 | A | 0 |
| 85 | 541 | 16.6 | 16.85 | −28.31 | A | 0 |
| 71 | 665 | 20.7 | 21 | −41 | A | 0.5 |
| 74 | 1690 | 31.15 | 31.45 | −38.31 | A | 0.5 |
| 78 | 688 | 21.65 | 21.95 | −34.97 | A | 0.5 |
| 80 | 640 | 19.7 | 19.95 | −33.74 | A | 0.5 |
| 82 | 1225 | 32.3 | 32.55 | −30.07 | B | 0.5 |
| 83 | 867 | 20.5 | 20.75 | −29.56 | A | 0.5 |

The results of 205 m/z-intensity pairs having different levels in spectra from the two sample sets were analyzed by examining graphs. FIG. 10 provides four examples of the graphs that could be examined. Twenty-two results were identified (in pairs) as components of possible full-shift false positives (a shift in which the rising and falling edge of signals shifted in time were both identified as differences), and 76 were identified as possible half-shift false positives (in which only one edge was identified as a difference). One hundred and six results were not identified as possible false positives.

The observed shifts were tightly clustered around a shift of one time bin (with the B condition eluting later than the A condition). The analysis was re-run taking this shift into account. In this analysis, only 113 differences were found. Six of these were identified as possible half shifts; no full shifts were identified. The results are largely consistent with those of the analysis that used no shift in elution times. Almost all the results in the shifted analysis were present in the analysis conducted without the shift. Twenty results that were not identified as possible false positives in the initial analysis vanished in the shifted analysis, but they tended to be weak results (13 of them appeared later than the hundredth entry). A few new weak results showed up in the shifted analysis as well.

Spectra from a single sample set were compared to each other to determine the likelihood that apparent differences were generated when none should exist. Eight spectra from condition A, in two sets of four, were compared, with no sample repeated either within a group of four or between the two groups. One hundred pairs of subsets were randomly selected (out of a possible 8!=40320 possibilities) and each pair was analyzed for differences. Among the 100 results, no differences were found in more than half; the third quartile ($75^{th}$ percentile) of number of differences is 1.

Thus, the number of false positives is expected to be low in general. A few pairs of subsets gave rise to 13 or 15 differences, and the total number of false positives over the 100 subset pairs was 196. The false positive rate could be estimated at roughly 2 per analysis.

Example 3

Quantitation of Protein Abundance Differences

It is sometimes useful to be able not only to detect changes in protein abundance, but to estimate the amount by which the abundance of detected proteins has changed. An experiment with a protein mixture was carried out to illustrate quantitation of relative changes in protein abundance.

The base mixture was as in Example 2, with BSA spiked into condition A at a concentration of 0.06 pmol/microliter, and into mixture B at a concentration of 0.03 pmol/microliter for a 2-fold change in protein abundance between the two samples.

Table 4 gives three examples of these calculations, for three different detected differences (see also FIGS. 1–9). Values based on normalized and unnormalized intensities using methods based on the ratio of area under curve or the difference of area under curve of logarithms of intensities are given. All three differences arise from bovine serum albumin, which was spiked into conditions A and B at putative concentration ratio of 2:1.

TABLE 4

| m/z | Start (minutes) | end (minutes) | Ratio of unnormalized values | Difference of unnormalized logarithms | Ratio of normalized values | Difference of normalized logarithms |
|---|---|---|---|---|---|---|
| 508 | 16.25 | 16.75 | 2.7 | 3.2 | 2.8 | 3.2 |
| 609 | 16.55 | 17.0 | 2.4 | 2.6 | 2.3 | 2.5 |
| 1230 | 37.2 | 37.5 | 2.8 | 2.9 | 2.7 | 2.8 |

Example 4

Analysis of a Myoglobin Digest by Comparison with a Blank

The techniques described herein were applied to compare LCMS data taken from a myoglobin digest to LCMS data obtained from a blank sample. Five data sets were obtained for each. These results were compared to results from a spiking experiment similar to the one described in Example 2, but with myoglobin spiked into sample A at a concentration of 0.625 pmol/microliter, and not present in sample B. The concentration of the spiked digest was 1 pmol/microliter.

Using the test involving finding the mean and variance of the underlying distribution of logarithms by the method of moments, thirty-six significant differences were found between the blank and the myoglobin digest. Of these, 18 were detected (with the same m/z value and greater than 50% overlap in retention times) in the comparison between a peptide mixture with and without myoglobin digest. The 18 differences not found in the peptide-mixture comparison are smaller than the differences that were found. For example, if we look at the area under the average intensity curve, we find that in the group that was not found in the peptide-mixture comparison, the median difference in area under the curve in the region of significant difference is 114800 in arbitrary intensity units (interquartile range 66210–156100), while for the group that was found, the median difference is 210200 (interquartile range "iqr" 173400–689600). Similarly, if we look at the maximum value of the average intensity curve, we find that the median value is 23180 (iqr 15740–34380) in the group found only in the spikes vs. blank comparison, and 45370 (iqr 28540–101860) in the group found in the comparison of peptide mixtures as well. Two of the differences not found in the comparison of peptide mixtures are extremely small, and may be false positives.

The concentration of myoglobin in the blank vs. myoglobin digest comparison was 50 times greater than the concentration in the peptide-mixture comparison. Differences that were small in the more concentrated digest were not detected when the material was less concentrated.

TABLE 5

| | Peptide mixture comparison | | Blank vs. myoglobin comparison | | |
|---|---|---|---|---|---|
| m/z | Start | end | Start | end | Difference in AUC |
| 804 | 29.85 | 31 | 29.9 | 30.75 | 3763788 |
| 805 | 29.85 | 30.9 | 29.95 | 30.55 | 1107230.8 |
| 637 | 27.3 | 28.2 | 27.5 | 28 | 1049923.6 |
| 992 | 24.95 | 25.55 | 25.05 | 25.45 | 419098.6 |
| 662 | 25.05 | 25.5 | 25.05 | 25.5 | 195797.4 |
| 690 | 39.35 | 40.25 | 39.65 | 40.6 | 1775206.2 |
| 691 | 39.35 | 40.25 | 39.75 | 40.25 | 303373.6 |
| 728 | 22 | 22.75 | 22.05 | 22.8 | 779753.6 |
| 729 | 22 | 22.7 | 21.75 | 22.65 | 160251.6 |
| 759 | 21.9 | 22.6 | 22.1 | 22.55 | 177572.2 |
| 834 | 30 | 30.6 | 30.25 | 30.65 | 150977.2 |
| 833 | 30.15 | 30.7 | 30.2 | 30.5 | 197830 |
| 724 | 24.85 | 25.15 | 24.75 | 25.15 | 103044.4 |
| 928 | 25.05 | 25.55 | 25.05 | 25.5 | 411672.2 |
| 816 | 30.3 | 30.55 | 30.05 | 30.65 | 174529.8 |
| 957 | 25.1 | 25.65 | 24.95 | 25.25 | 127588.8 |
| 1021 | 24.95 | 25.3 | 24.85 | 25.5 | 222555.4 |
| 757 | 21.95 | 22.5 | 21.85 | 22.5 | 173054.8 |

Differences found in both the peptide mixture comparison and in the blank vs. myoglobin comparison. The difference in area under the curve is provided for the blank vs. myoglobin case, for comparison with Table 6. Intensity units are arbitrary and therefore not comparable between experiments, so the difference in area under the curve is not reported for the peptide mixture comparison. Comparisons between myoglobin digest and blank are performed after transforming means and variances of intensities to imputed means and variances of the distribution of logarithm of intensity, as in Box 206 of FIG. 2.

TABLE 6

| m/z | Start | End | Difference in AUC |
|---|---|---|---|
| 853 | 22.25 | 22.5 | 31076.8 |
| 1003 | 25.1 | 25.55 | 110788.6 |
| 1035 | 30.3 | 30.55 | 28509 |
| 636 | 27.45 | 28.1 | 976545.6 |
| 1056 | 25.05 | 25.4 | 114790.2 |
| 681 | 25.05 | 25.35 | 117829 |
| 661 | 25.05 | 25.45 | 155593.2 |
| 619 | 25.1 | 25.5 | 156205.4 |
| 750 | 22.15 | 22.45 | 88542.6 |
| 666 | 27.35 | 27.8 | 124954 |
| 665 | 27.25 | 27.95 | 180066 |
| 650 | 25.3 | 25.7 | 230785.4 |
| 1058 | 25 | 25.25 | 46865.2 |
| 704 | 25 | 25.35 | 114802.8 |
| 672 | 25.35 | 25.6 | 65832.2 |
| 748 | 32.15 | 32.8 | 368706.8 |
| 1043 | 25.05 | 25.4 | 67347.8 |
| 1086 | 25 | 25.3 | 47210.6 |

Differences found only in the blank vs. myoglobin comparison, for comparison with Table 5.

Example 5

Analysis of Clinical Serum Samples using Mass Spectrometry Without Index

This example illustrates analysis of spectra not containing an index variable, and the identification of biomarkers. Data was downloaded from the web site http://clinicalproteomics.steem.com/download-ovar.php. Petricoin et al., Lancet 359:572–577, 2002, describe the use of the data to identify cancer biomarkers using a different analysis technique.

Data was analyzed using the steps in the even-numbered boxes in FIGS. 1A and 2, answering no at 106, 108, 112, and 136, and not performing the functions of 130, 132, and 134. The analysis used a window of m/z values within 0.5 units (and 0.25 units) on either side of each named value, referred to as bin width 1 (and bin width 0.5, respectively). For the analyses described below, results for the two bin widths differ quantitatively, but not qualitatively.

The significance of each and every m/z identifier in the data set was calculated. Use of pattern recognition methods and the signals identified allowed creation of a perfect predictor of disease state which uses only a handful of these signals. (A "perfect predictor" distinguishes cancer from control samples without error in both a set of training data and an independent test set).

In this analysis, two thirds of the cancer spectra and two thirds of the control spectra were randomly selected as a training set, and the remaining third was used as a test set. The method identified significant differences between cancer and control chromatograms in the signals associated with 6381 m/z identifiers, compared to 15,200 identifiers in the original set. Differences at 6925 identifiers were significant at bin width 0.5. When the exact identifiers in the original set were used with no binning, signals associated with 7884, or roughly half, were found to significantly differ between the two conditions.

Figure 15:
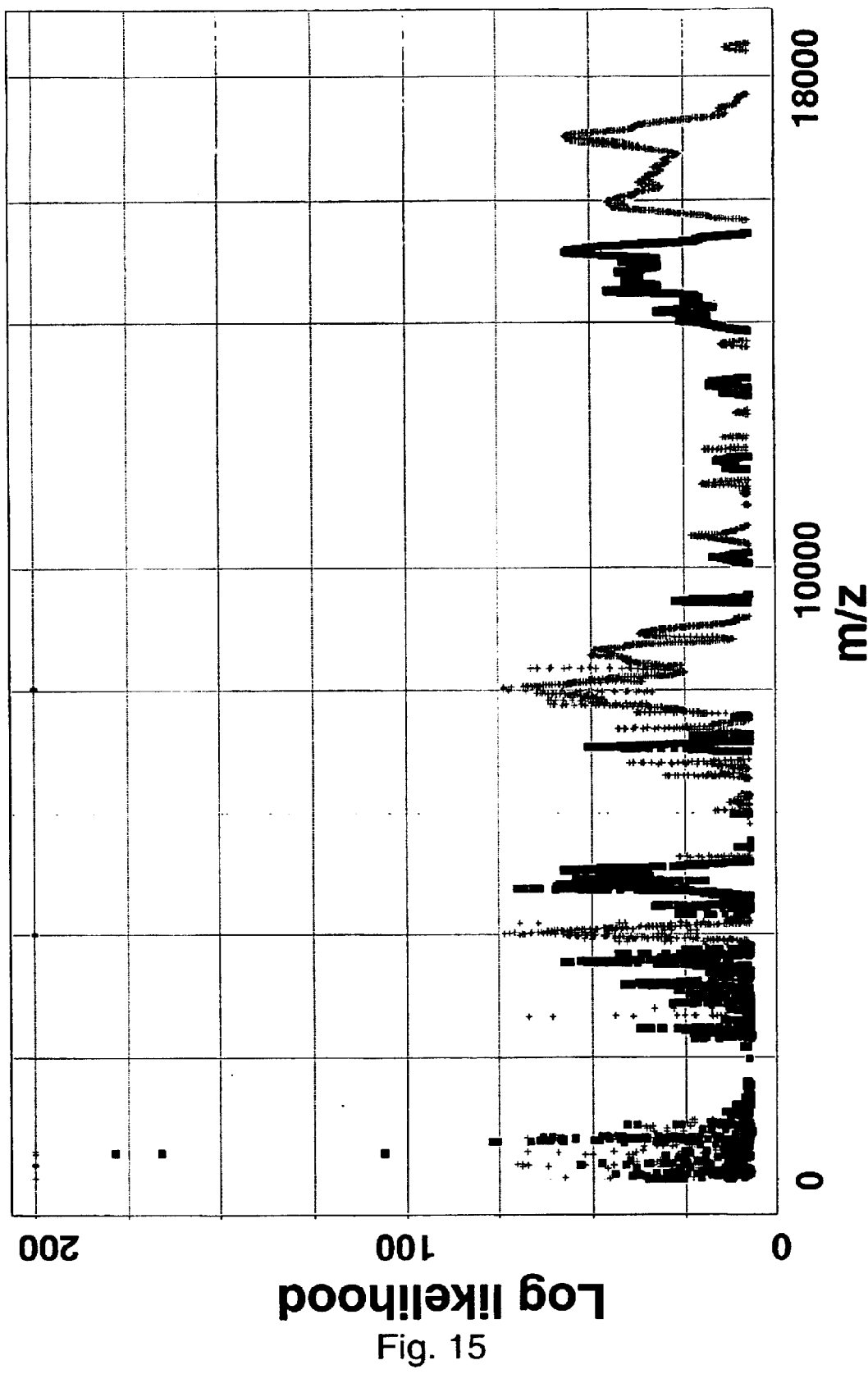
FIG. 15 shows m/z identifiers associated with signals showing significant differences between cancer and non-cancer samples. Horizontal axis: m/z (ranging from 0 to 19000; grid lines every 2000). Vertical axis: negative log likelihood (ranging from 0 to 100 in each panel; grid lines every 20); more positive values correspond to more significant differences. Negative log-likelihoods greater than 90 have been plotted at 100 for visibility. Darker squares show m/z identifiers associated with signals higher in cancer samples; lighter circles show m/z identifiers associated with higher signals in non-cancer samples. Pairs of results, for example at m/z 4000 and m/z 8000, may correspond to the same peptide at charges z=1 and z=2 or to monomer and dimer configurations of a peptide.

FIG. 15 shows the 6381 m/z identifiers associated with signals showing significant differences between cancer and non-cancer samples, plotted against the significance (negative log-likelihood) of each result. Higher negative log-likelihood indicates greater significance. Darker squares show m/z identifiers associated with signals that are higher in cancer than in non-cancer samples; lighter circles show m/z identifiers associated with signals that are higher in non-cancer than in cancer samples. The fact that broad peaks of significant identifiers are visible may reflect poor m/z resolution of the data. In several cases results appear to correspond to singly or doubly charged states or monomer or dimer configurations of the same analyte, which could give additional confidence in the results or aid in their interpretation or use for biomarker identification.

The fact that the peaks are broader for higher m/z identifiers might also in part reflect the fact that the measured m/z values are more broadly spaced in higher ranges. It also probably reflects the resolution characteristics of the instrumentation used to generate the data. This could be addressed either by deconvolving (using well established methods) the peaks in this p-value plot to find the central, or source, m/z identifiers for each peak, or using wider bins for higher m/z ranges. The resulting m/z identifiers and combined (by statistics or AUC or other common methods) intensities might then be more reliable for use as biomarkers.

If the means of two distributions of signals are not distinguishable, individual signals from those distributions can be less likely to be sufficiently different to differentiate cancer from control chromatograms than are signals for which the means are distinguishable. Thus, signals corresponding to the identified m/z identifiers are promising candidates for individual biomarkers.

It requires substantial computational effort to sort through 6381 sets of signals to figure out which subsets can be used to distinguish cancer from control samples. Classification trees (T. Hastie, R. Tibshirani & J. Friedman. The Elements of Statistical Learning. Springer Series in Statistics. Springer, New York, 2001) were created using the m/z identifiers with individual p-values in the top 5% of the distribution of p-values. Signals with the most distinguishable means are the most likely to allow creation of good classifiers, for the same reasons that signals with distinguishable means are more likely to be good individual biomarkers.

A simple tree with splits using signals at only three m/z identifiers, 246, 435, and 25, achieves perfect classification of the training set, and misclassifies one cancer and one control in the test set. The signals at m/z 246 are the single best classifier, these signals alone classify the training set with only 3 errors in the training set (one cancers and two controls misclassified) and 6 errors in the test set (one cancer and five controls misclassified).

Because all three of the m/z values in the best classification tree were small (and therefore potentially associated with the matrix in which the sample was embedded for analysis, rather than with the sample itself), additional classification trees were constructed with the constraint that only m/z identifiers greater than or equal to some value were permitted. When only m/z identifiers greater than 400 are permitted, the identifiers 435, 417, 419, and 463 are used. The training set is perfectly classified, but 2 controls are misclassified in the test set. Each of these identifiers is less than 500. When only m/z values greater than 500 are allowed, a classification tree is constructed using the m/z values 618, 681, 3991, 3992, 4004, 4746, 4820, and 7995. The training set is perfectly classified, and in the test set 4 cancers and 4 controls are misclassified. Thus in this data set good classification performance seems to be easier to achieve using low m/z identifiers.

The signal identified as the best single identifier (246) is not listed by the web site providing the data as part of the set providing perfect classification, and therefore may be a novel discovery.

Another way to assess the importance of different m/z identifiers is to construct a random forest (Breiman, L. (2001), Random Forests, Machine Learning 45(1), 5–32). A random forest is a collection of classification trees, in which randomness is introduced both in the data used by each tree (through bootstrap sampling of the data) and in the variables eligible to be used for classification at each step in building each tree. Classification is by plurality vote of the constituent trees of the forest. If a sufficiently large forest is generated, each variable is considered as a classifying feature many times with many different subsets of the data. It is therefore possible to assess each variable's importance, that is, how much the overall result is influenced by each individual variable. When variable importance is checked using bin widths of 1 and 0.5 and for the exact identifiers in the data set, the results are broadly consistent. A cluster of variables with m/z identifiers near 245 were most important in each case, followed by m/z identifiers near 435 and 465. Thus, these variable importance results were consistent with the analyses using single classification trees.

Other embodiments are within the following claims. While several embodiments have been shown and described, various modifications may be made without departing from the spirit and scope of the present invention.

What is claimed is:

1. A mass spectrometry method for identifying differences in the level of one or more analytes between two or more sample sets comprising the steps of:
   (a) obtaining spectra for individual samples of said two or more sample sets, wherein said spectra comprise m/z-intensity pairs, wherein an m/z intensity pair comprises an m/z identifier and a signal associated with said m/z identifier,
   (b) for each said m/z identifier of one or more m/z identifiers from said m/z intensity pairs, determining a relationship between the corresponding signals in said spectra, and
   (c) assigning each said relationship a rank or value based on both within-sample-set and between-sample-set signal distributions, wherein said rank or value is a measure of a likelihood that said signal arises from an analyte having a different level between said two or more sample sets.

2. The method of claim 1, wherein said relationship is determined for at least 100 different m/z identifiers.

3. The method of claim 1, wherein said second sample set is a standard.

4. The method of claim 1 wherein each of said different m/z identifiers is deterministically specified prior to said step (b).

5. The method of claim 2, wherein said m/z identifiers comprise substantially all of the m/z identifiers from said spectra.

6. The method of claim 1, wherein said step (c) relies on a parametric representation of the distribution.

7. The method of claim 1, wherein said step (c) relies on a non-parametric representation of the distribution.

8. The method of claim 6, wherein said step (c) comprises determining the statistical significance of the difference between measures of central tendency of said distributions in light of the variability of said distributions.

9. The method of claim 8, wherein said central tendency is mean.

10. The method of claim 9, wherein the statistical significance is calculated using a t-test.

11. The method of claim 8, wherein said m/z-intensity pairs further comprises one or more index values associated with said signal and said identifier and said relationship is determined taking into account said one or more index values.

12. The method of claim 11, wherein the m/z-intensity pairs are aligned along the index variable(s).

13. The method of claim 12, wherein said method further comprises normalization of data prior to said step (b).

14. The method of claim 13, wherein signals in a set of spectra are aligned by aligning one or more landmarks, where each of said landmarks is a peak at a particular m/z identifier and at a particular set of values of index variables.

15. The method of claim 14, where said landmarks are found in the data by a method comprising identifying peaks that occur in all spectra in a spectra set at the same m/z identifier and at nearly the same set of index variables, optionally smoothing the intensities as a function of index variables, and using as the landmarks the set of index variable values at which the largest smoothed intensity values occur.

16. The method of claim 15, wherein said spectra are aligned by shifting the set of index variable values associated with each of said landmarks to the set of index variable values associated with said landmarks in some reference spectrum, and intermediate index values are assigned by interpolation.

17. The method of claim 1, wherein significant differences at a set of m/z values are grouped together as features if at least j out of k consecutive m/z identifiers have significant differences for a particular common set of index variables, where j and k are user-specified integers with j less than or equal to k.

18. The method of claim 17, wherein said sufficiently wide is defined by said m/z's span being a range greater than or equal to a specified fraction of the largest m/z in the set to be grouped.

19. The method of claim 13, wherein said significance requires significance over at least m out of n consecutive index variable values where m and n are user-specified integers with m less than or equal to n.

20. The method of claim 14, wherein signals in different sets of spectra are aligned by aligning expected signals from agents specially spiked into the samples.

21. The method of claim 1, wherein said relationship in analyte abundance is further quantified by first calculating an integrated signal for each condition in a region containing the significant change, and then comparing the integrated signals and using the resulting relationship as indicative of relative analyte abundances.

22. The method of claim 8, wherein identified differences are grouped to indicate those putatively arising from different charge states and/or isotopes of a single analyte.

23. The method of claim 8, further comprising performing one or more iterations to reduce false positives.

24. The method of claim 23, comprising filtering said list for false positives by finding for each identified difference the index-variable shift that minimizes some measure of distance between the intensity profiles for the two conditions and determining whether the difference is still significant after said index-variable shift, then eliminating differences that are not significant after said index-variable shift.

25. The method of claim 13, wherein said normalization comprises, for each spectrum and each combination of index variables, finding a measure of central tendency of a specified subset of the signals, and dividing all the intensity values by that measure of central tendency.

26. The method of claim 8, wherein at least 3 different spectra are obtained for each sample set.

27. The method of claim 26, wherein at least 5 different spectra are obtained from each sample set.

28. The method of claim 27, wherein each of said 5 different spectra is from different samples.

29. The method of claim 26, wherein said two or more sample sets are biological samples.

30. The method of claim 29, wherein said one of more analytes are peptides or metabolic by-products.

31. The method of claim 29, wherein said measurements are obtained by coupling a surface phase separation with mass spectrometry.

32. The method of claim 29, wherein said sample sets are characterized by one of more of the following: different doses of an administered agent, the presence of a disease or disorder, different types of treatment, different genetic or epigenetic attributes, or different levels of a particular disease or disorder.

33. The method of claim 29, wherein said measurements are obtained by coupling one- or multi-dimensional liquid chromatography with mass spectrometry.

34. A computer program comprising instructions on a computer readable medium for performing steps (b) and (c) of claim 1.

* * * * *